(12) United States Patent
Sauer

(10) Patent No.: US 10,631,853 B2
(45) Date of Patent: Apr. 28, 2020

(54) SUTURE SECURING TUBE AND ASSEMBLY THEREOF

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 314 days.

(21) Appl. No.: 15/726,721

(22) Filed: Oct. 6, 2017

(65) Prior Publication Data
US 2019/0105034 A1  Apr. 11, 2019

(51) Int. Cl.
| | | |
|---|---|---|
| *A61B 17/04* | (2006.01) |
| *A61B 17/22* | (2006.01) |
| *A61B 17/12* | (2006.01) |
| *A61B 17/00* | (2006.01) |
| *A61B 17/11* | (2006.01) |
| *A61B 17/06* | (2006.01) |
| *A61B 17/34* | (2006.01) |
| *A61B 17/132* | (2006.01) |
| *A61B 17/122* | (2006.01) |

(52) U.S. Cl.
CPC ...... *A61B 17/0485* (2013.01); *A61B 17/0482* (2013.01); *A61B 17/122* (2013.01); *A61B 17/06133* (2013.01); *A61B 17/12013* (2013.01); *A61B 17/1322* (2013.01); *A61B 2017/0042* (2013.01); *A61B 2017/0046* (2013.01); *A61B 2017/00292* (2013.01); *A61B 2017/00349* (2013.01); *A61B 2017/00358* (2013.01); *A61B 2017/00473* (2013.01); *A61B 2017/0477* (2013.01); *A61B 2017/1142* (2013.01); *A61B 2017/12018* (2013.01); *A61B 2017/3419* (2013.01)

(58) Field of Classification Search
CPC ............ A61B 17/0485; A61B 17/0482; A61B 17/0469; A61B 17/06061; A61B 17/0467; A61B 17/0483; A61B 17/0487
See application file for complete search history.

(56) References Cited

U.S. PATENT DOCUMENTS

| | | |
|---|---|---|
| 3,877,434 A | 4/1975 | Ferguson |
| 4,177,813 A | 12/1979 | Miller |
| 8,535,301 B2 | 9/2013 | Cox et al. |
| 2016/0030159 A1* | 2/2016 | Ticker .................. A61F 2/0811 606/232 |
| 2016/0324527 A1 | 11/2016 | Thompson |

OTHER PUBLICATIONS

Jul. 18, 2016 Web Page; http://veteriankey.com/vascular-surgery/; Phillips, Heidi , Vascular Surgery: Veterian Key Website, copyright Jul. 18, 2016, with particular reference to the Rumel tourniquet comments and pictures highlighted on pp. 3 and 4, which are apparently from a 1993 publication.
Nov. 25, 2015 Web Page; http://www.surgecardiovascular.com/products/Tourniquets.aspx, Surge Cardiovascular: Tourniquets.

* cited by examiner

*Primary Examiner* — Katrina M Stransky
(74) *Attorney, Agent, or Firm* — David J. Gervasi; Christopher B. Miller

(57) ABSTRACT

A distal tip for a suture securing tube is disclosed. The distal tip has a flared distal end and a distal opening in the flared distal end. The distal tip also has a tube interface opening in a proximal end. The distal tip further has a channel coupling the distal opening to the tube interface opening. The distal tip also has one or more crimp windows.

9 Claims, 30 Drawing Sheets

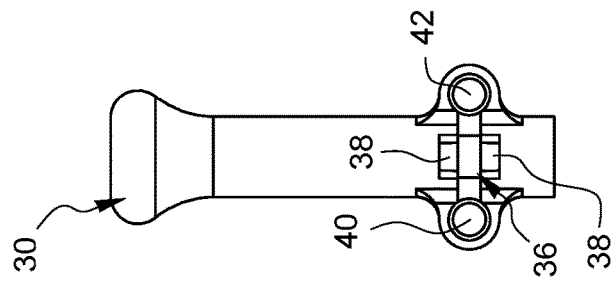
FIG. 2D
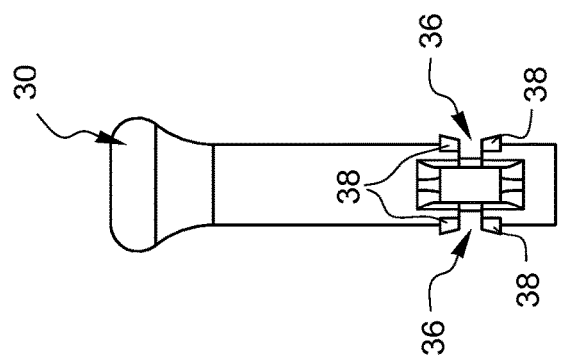
FIG. 2C
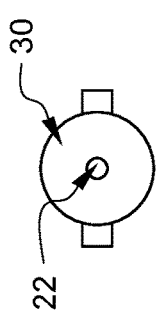
FIG. 2E
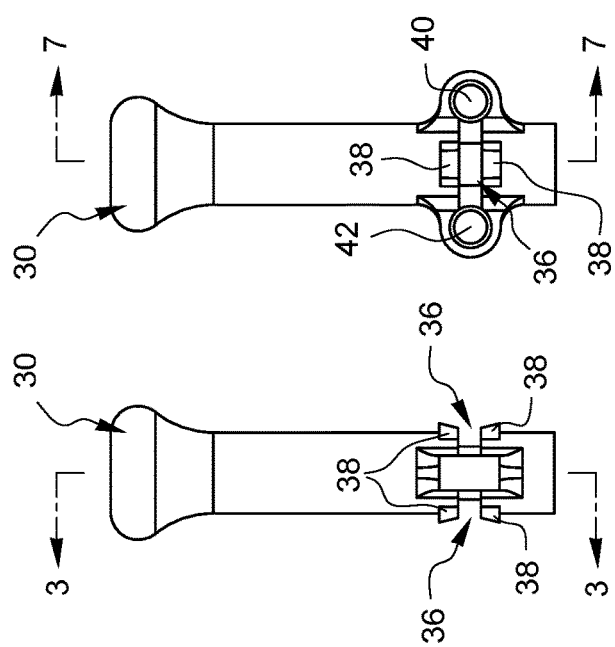
FIG. 2A
FIG. 2B
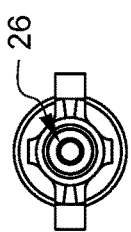
FIG. 2F

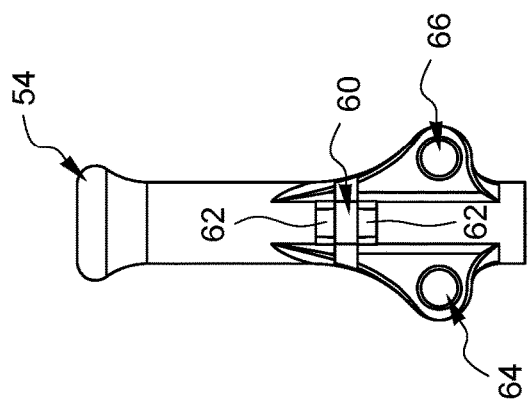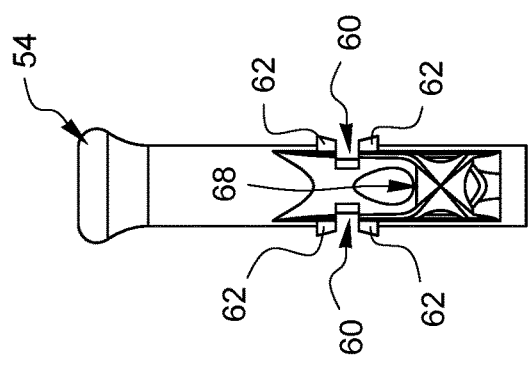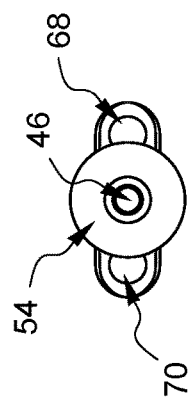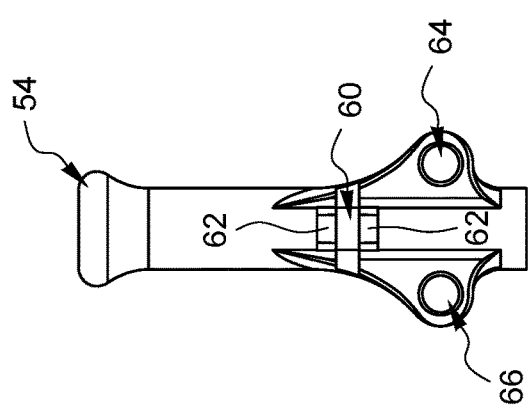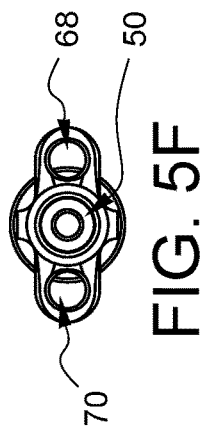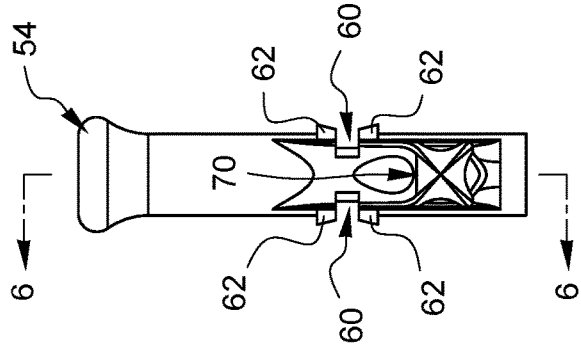

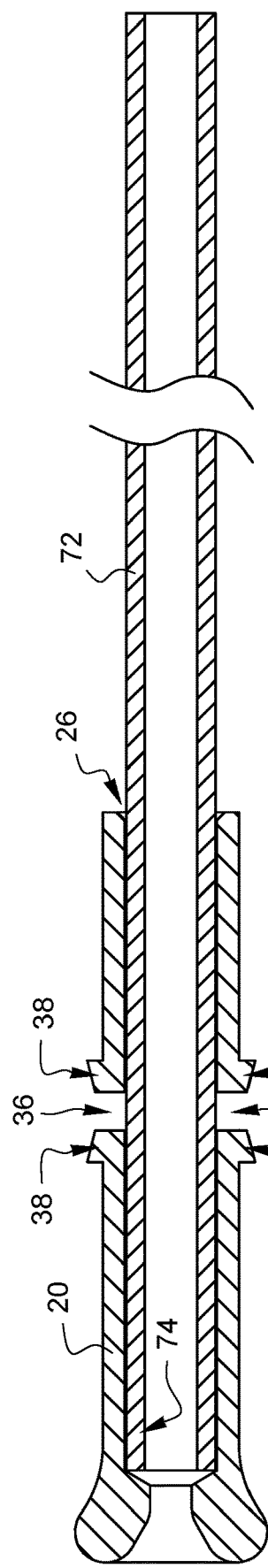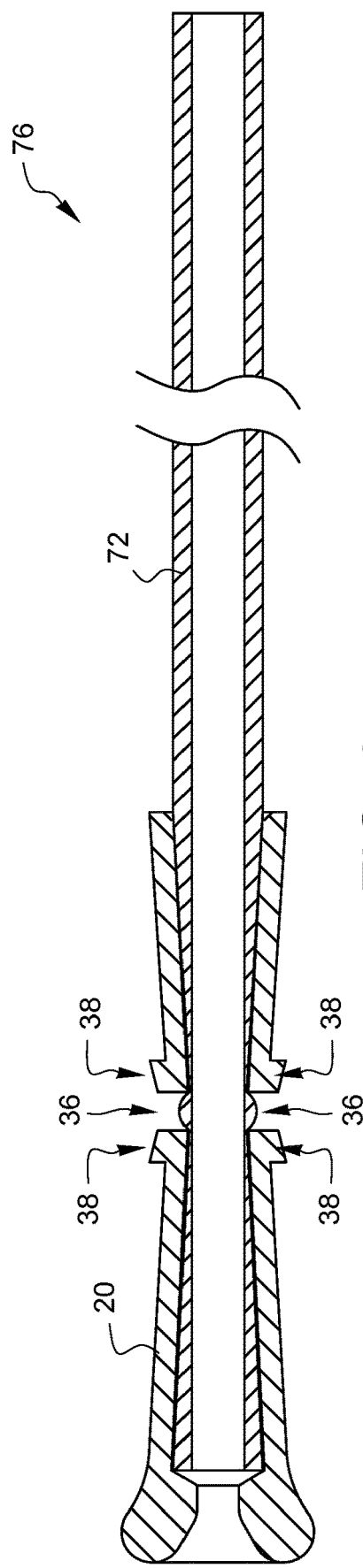

SUTURE SECURING TUBE AND ASSEMBLY THEREOF

FIELD

The claimed invention relates to surgical implements, and more specifically to a versatile and improved tube to facilitate the securing of sutures during a surgical procedure.

BACKGROUND

Various types of surgery require a surgeon to place and temporarily secure a suture during a given surgical procedure. For example, prior to cannulation in cardiac surgery, surgeons often place one or more pursestring sutures around a target tissue site before an incision will be made for a cannula to be inserted. Then, after the incision is made at the target site and the cannula has been inserted, the one or more pursestring sutures are cinched to pull the tissue closed around the cannula to ensure there is a good seal around the cannula. Since the cannula will be removed before the end of the procedure, it is not efficient to tie a knot in the suture ends. Furthermore, given the increase in minimally invasive surgical techniques, the surgical team may not have direct access to the suture ends exiting the tissue, so it can be difficult to maintain a cinched pressure around the cannula.

One solution employed by surgeons in this situation is the use of a simple tube. The suture ends in need of temporary cinching are passed through a thin tube which reaches from the surgical site to a convenient location away from the surgical site. The distal end of the tube presses against the tissue where the sutures exit the tissue and, while holding the proximal end of the tube, the suture ends are pulled out of the proximal end of the tube to create a desired tension. Then, the proximal end of the tube is clamped to hold the sutures until it is time to release them. While workable, there is much room for improvement with these types of tube tourniquet solutions. It would be desirable to have an improved suture securing tube that reduces tissue trauma on the distal end, is more compatible with the limited space constraints presented in minimally invasive surgical techniques, and which provides additional options for the temporary securing of the suture ends passing out of the proximal end.

BRIEF DESCRIPTION OF THE DRAWINGS

FIGS. 2A, 2B, 2C, 2D, 2E, and 2F are top, left, right, bottom, distal, and proximal elevational views, respectively, of the distal tip from FIGS. 1A and 1B.

FIGS. 5A, 5B, 5C, 5D, 5E, and 5F are top, left, right, bottom, distal, and proximal elevational views, respectively, of the distal tip from FIGS. 4A and 4B.

FIGS. 7 and 8 are side cross-sectional views schematically illustrating one example of how the distal tip of FIG. 1A is crimped onto a tube.

DETAILED DESCRIPTION

Figure 1A:
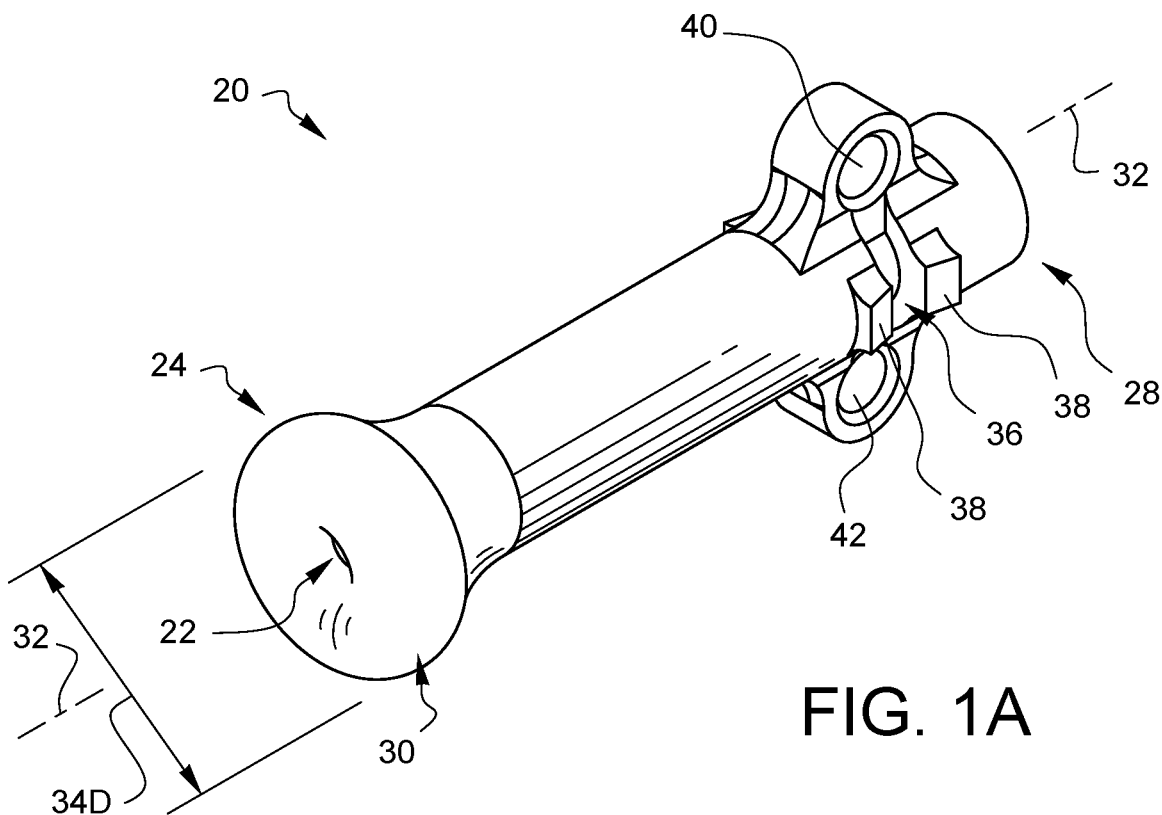
FIG. 1A is a perspective view of one embodiment of a distal tip shown from a distal perspective.
Figure 1B:
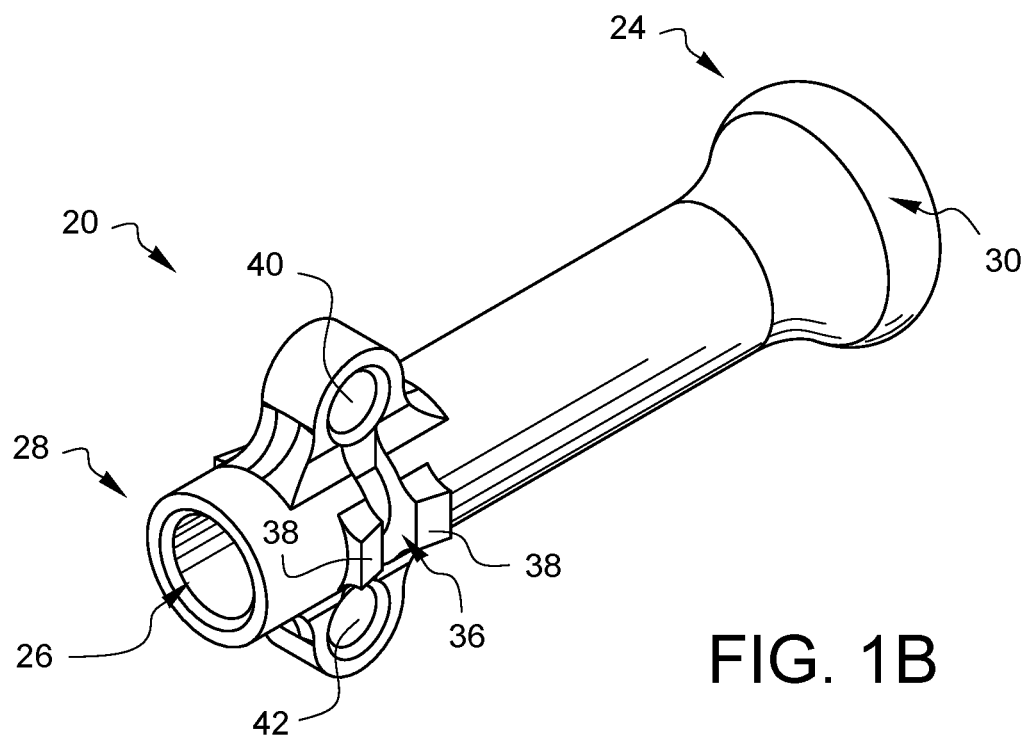
FIG. 1B is a perspective view of the distal tip of FIG. 1A from a proximal perspective.

FIG. 1A is a perspective view of one embodiment of a distal tip 20, shown from a distal perspective, for a suture securing tube (not shown in this view). FIG. 1B is a perspective view of the distal tip 20 of FIG. 1A, shown from a proximal perspective. A distal opening 22 is located in the distal end 24 of the distal tip 20. A tube interface opening 26 is located in the proximal end 28 of the distal tip 20. The distal tip 20 has a channel which communicates between the distal opening 22 and the tube interface opening 26. The distal end 24 of the distal tip 20 has a flared end 30 which has a radius configured to reduce tissue trauma when the distal end 24 of the distal tip 20 is pressed against tissue. As one example, the cross-sectional radius of the flared end 30

(taken on a plane in which the longitudinal axis 32 of the distal tip 20 lies) is larger than the cross-sectional radius of the tube edges of the tube (not visible in this view) which will be mated with the tube interface opening 26. As another example, the diameter 34D of the flared end 30 may be larger than the diameter of the tube (not visible in this view) which will be mated with the tube interface opening 26. Other embodiments may have other definitions of how the flaring of the flared end 30 reduces tissue trauma vs a simple tube, and the definition of the flared end 30 does not need to be determined based on a comparison with the tube (not visible in this view). As one example, the flared end 30 could simply be flared with respect to the adjacent portion of the distal tip 20.

The distal tip 20 also has crimp windows 36 located between crimp directors 38. As will be discussed in more detail later in this specification, when pressure is applied to the crimp directors 38, the inner edges of the crimp window 36 will pinch into a tube (not shown in this view), that has been placed in the tube interface opening 26, in order to secure the tube to the distal tip 20. Other embodiments might not have one or more crimp windows and/or one or more crimp directors, as the tube (not shown in this view) could be secured by other methods, including, but not limited to ultrasonic welding, gluing, press fitting, shrinking, melting, or threading. Still other embodiments might not have one or more crimp windows and/or one or more crimp directors because the tube (not shown in this view) could be formed continuously with the distal tip.

This embodiment of the distal tip 20 also defines two anchor channels 40, 42 through which one or more tie-down sutures (not shown) may be passed to hold the distal tip 20 in a particular orientation during a surgery in order to help keep a surgical field organized. For example, if the distal tip 20 of a suture securing tube is used in conjunction with pursestring sutures that are cinched against a cannula placed in an aorta during cardio-pulmonary bypass, a separate suture may be routed through the anchor channels 40, 42 of the distal tip 20 and secured around the cannula to keep the distal tip 20 and the tube (not shown in this view) in line with the cannula rather than allowing the distal tip 20 to flop away from the cannula. In the embodiment of FIGS. 1A and 1B, the anchor channels 40, 42 face a direction that is not parallel to the longitudinal axis 32 of the distal tip. Other embodiments may have different numbers of anchor channels or no anchor channels at all. Other embodiments may have one or more anchor channels which face in a different direction as compared to the anchor channels 40, 42 of FIGS. 1A and 1B.

FIGS. 2A, 2B, 2C, 2D, 2E, and 2F are top, left, right, bottom, distal, and proximal elevational views, respectively, of the distal tip 20 from FIGS. 1A and 1B.

Figure 3:
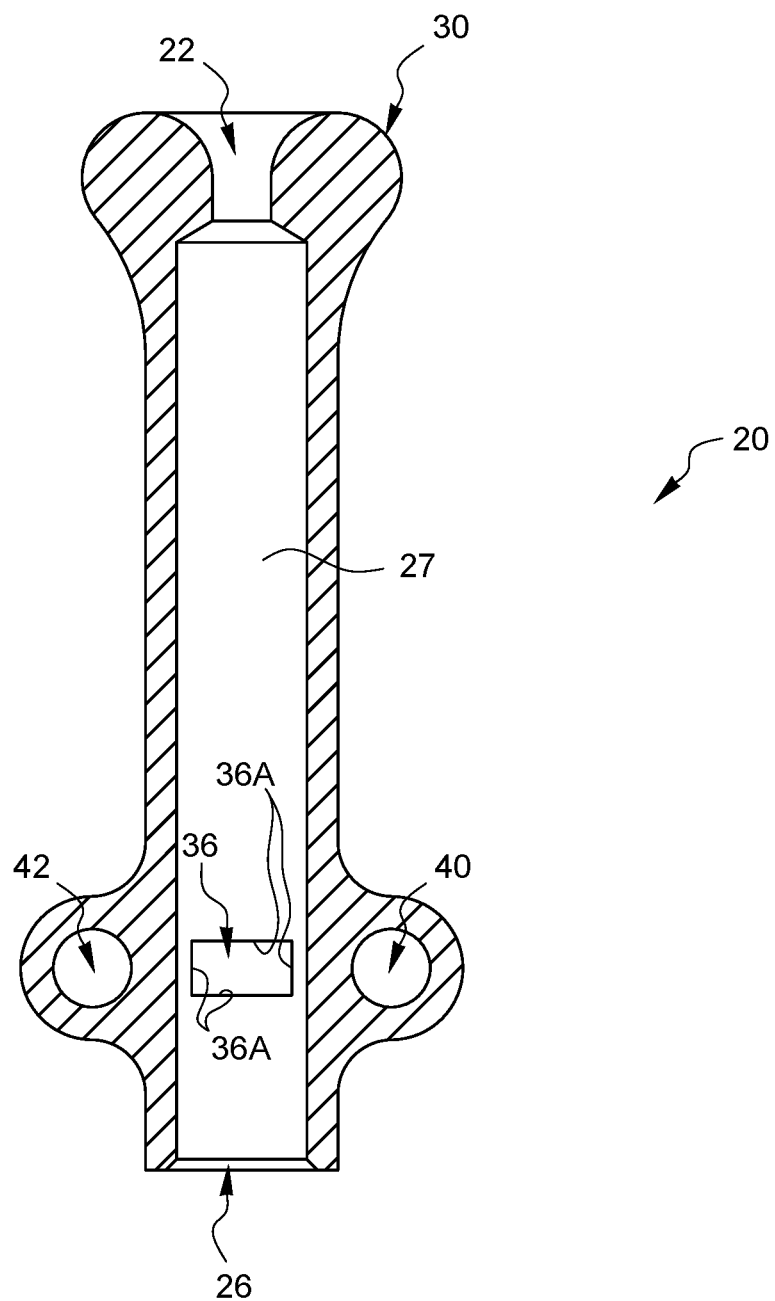
FIG. 3 is an enlarged side cross-sectional view of the distal tip 20 of FIGS. 1A and 1B.

FIG. 3 is an enlarged side cross-sectional view of the distal tip 20 of FIGS. 1A and 1B taken along line 3-3 from FIG. 2B. The inner edges 36A of one of the crimp windows 36 can be seen from the inside of the distal tip 20. The channel 27 which communicates between the distal opening 22 and the tube interface opening 26 can also be seen in this view.

Figure 4A:
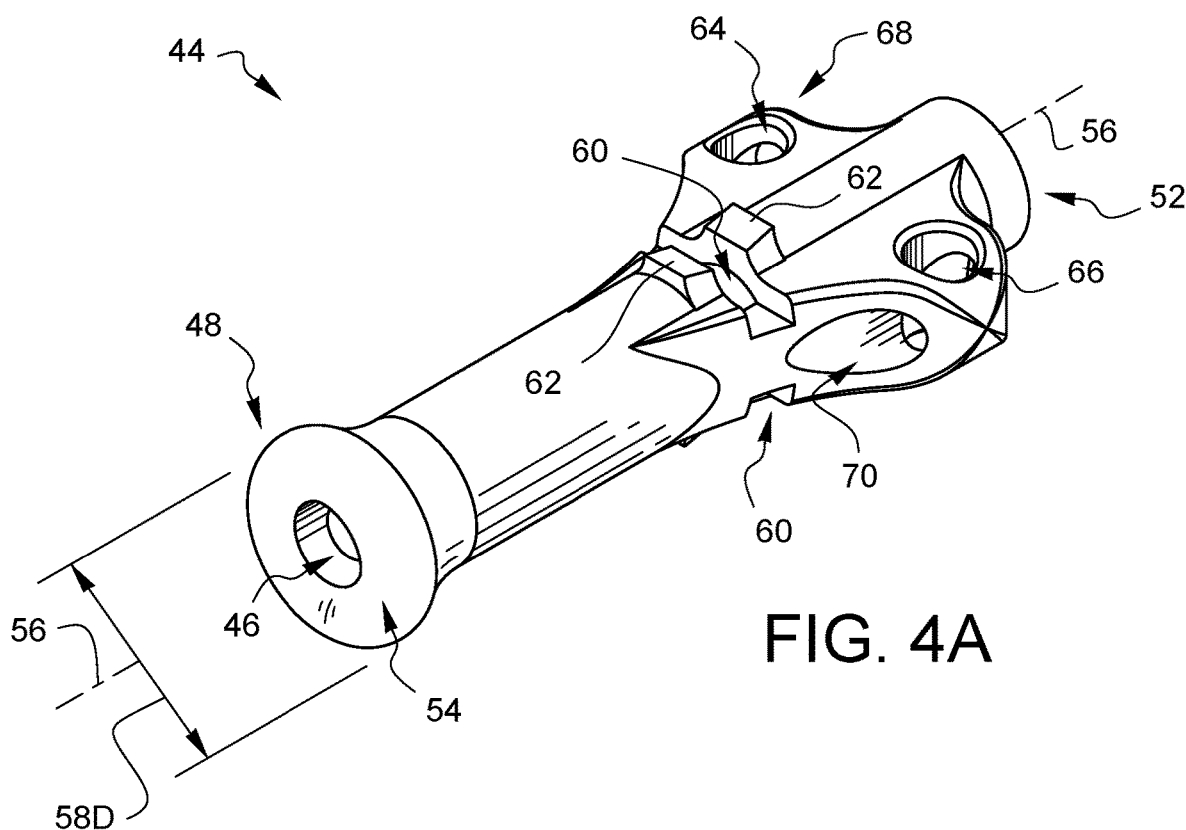
FIG. 4A is a perspective view of another embodiment of a distal tip, shown from a distal perspective.
Figure 4B:
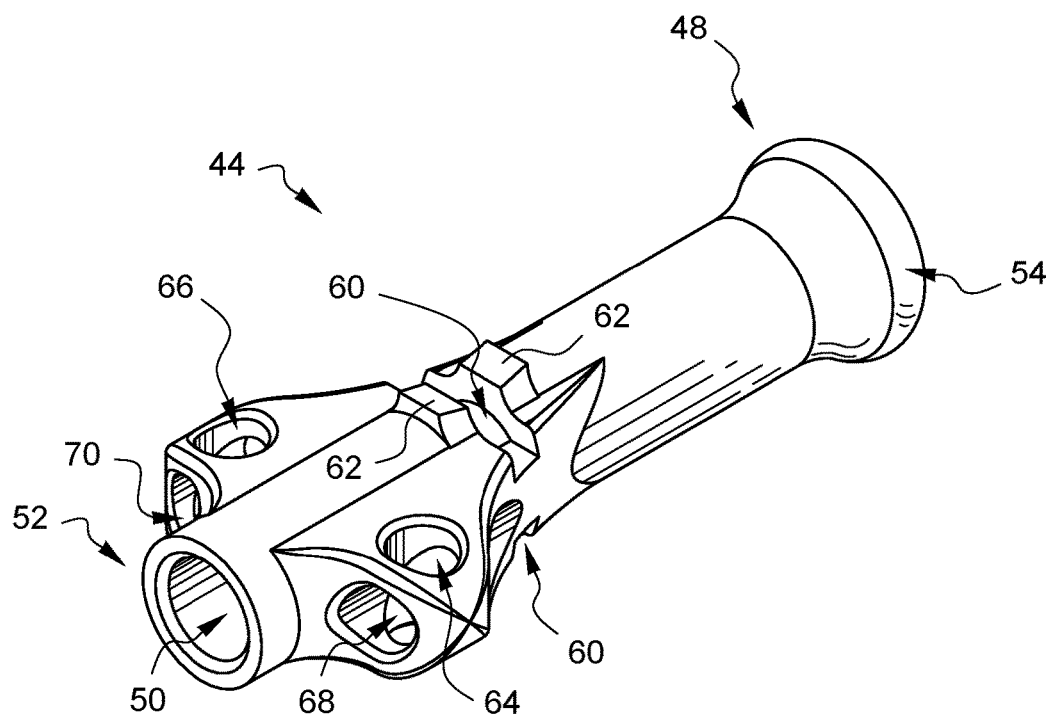
FIG. 4B is a perspective view of the distal tip of FIG. 4A, shown from a proximal perspective.

FIG. 4A is a perspective view of another embodiment of a distal tip 44, shown from a distal perspective, for a suture securing tube (not shown in this view). FIG. 4B is a perspective view of the distal tip 44 of FIG. 4A, shown from a proximal perspective. A distal opening 46 is located in the distal end 48 of the distal tip 44. A tube interface opening 50 is located in the proximal end 52 of the distal tip 44. The distal tip 44 has a channel which communicates between the distal opening 46 and the tube interface opening 50. The distal end 48 of the distal tip 44 has a flared end 54 which has a radius configured to reduce tissue trauma when the distal end 48 of the distal tip 44 is pressed against tissue. As one example, the cross-sectional radius of the flared end 54 (taken on a plane in which the longitudinal axis 56 of the distal tip 44 lies) is larger than the cross-sectional radius of the tube edges of the tube (not visible in this view) which will be mated with the tube interface opening 50. As another example, the diameter 58D of the flared end 54 may be larger than the diameter of the tube (not visible in this view) which will be mated with the tube interface opening 50. Other embodiments may have other definitions of how the flaring of the flared end 54 reduces tissue trauma vs a simple tube, and, as noted with the previous embodiment, the definition of the flared end 54 does not need to be determined based on a comparison with the tube (not visible in this view).

The distal tip 44 also has crimp windows 60 located between crimp directors 62. As will be discussed in more detail later in this specification, when pressure is applied to the crimp directors 62, the inner edges of the crimp window 60 will pinch into a tube (not shown in this view), that has been placed in the tube interface opening 50, in order to secure the tube to the distal tip 44. Other embodiments might not have one or more crimp windows and/or one or more crimp directors, as the tube (not shown in this view) could be secured by other methods, including, but not limited to ultrasonic welding, gluing, press fitting, shrinking, melting, or threading. Still other embodiments might not have one or more crimp windows and/or one or more crimp directors because the tube (not shown in this view) could be formed continuously with the distal tip.

This embodiment of the distal tip 44 also defines four anchor channels 64, 66, 68, and 70 through which one or more tie-down sutures (not shown) may be passed to hold the distal tip 44 in a particular orientation during a surgery in order to help keep a surgical field organized. For example, if the distal tip 44 of a suture securing tube is used in conjunction with a purse string suture that is cinched against a cannula placed in an aorta during cardio-pulmonary bypass, a separate suture may be routed through the anchor channels 64, 66 of the distal tip 44 and secured around the cannula to keep the distal tip 44 and the tube (not shown in this view) in line with the cannula rather than allowing the distal tip 44 to flop away from the cannula. In the embodiment of FIGS. 4A and 4B, the anchor channels 64, 66 face a direction that is not parallel to the longitudinal axis 56 of the distal tip 44. This embodiment also has anchor channels 68, 70 which face a direction that is substantially parallel to the longitudinal axis 56. These channels 68, 70 provide other anchoring options. Furthermore, in this embodiment, anchor channel 64 intersects anchor channel 68. Similarly, anchor channel 66 intersects anchor channel 70, enabling sutures routed into one anchor channel to be routed out of an intersecting channel, providing surgeons with even more options and flexibility for anchoring purposes. Other embodiments may have different numbers of anchor channels or no anchor channels at all. Other embodiments may have one or more anchor channels which face in a different direction as compared to the anchor channels 64, 66, 68, and 70 of FIGS. 4A and 4B.

FIGS. 5A, 5B, 5C, 5D, 5E, and 5F are top, left, right, bottom, distal, and proximal elevational views, respectively, of the distal tip 44 from FIGS. 4A and 4B.

Figure 6:
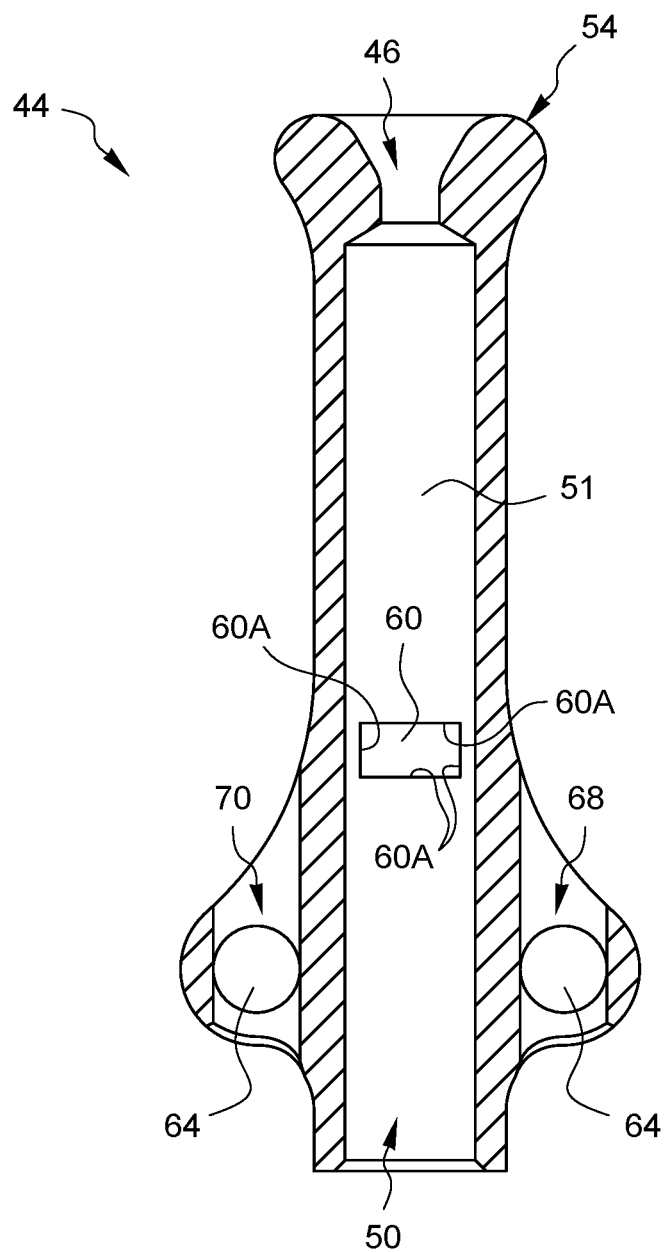
FIG. 6 is an enlarged side cross-sectional view of the distal tip of FIGS. 4A and 4B.

FIG. 6 is an enlarged side cross-sectional view of the distal tip 44 of FIGS. 4A and 4B taken along line 6-6 from FIG. 5B. The inner edges 60A of one of the crimp windows 60 can be seen from the inside of the distal tip 44. The channel 51 which communicates between the distal opening 46 and the tube interface opening 59 can also be seen in this view.

FIGS. 7 and 8 are side cross-sectional views schematically illustrating one example of how the distal tip 20 of FIG. 1A is crimped onto a tube 72. The distal tip 20, as shown in FIGS. 7 and 8, has been cross-sectioned along line 7-7 from FIG. 2A. As shown in FIG. 7, a proximal end 74 of the tube 72 has been inserted into the tube interface opening 26 of the distal tip 20. The proximal end 74 of the tube 72 is inserted past the crimp windows 36. A force is applied to the crimp directors 38 to push the crimp directors 38 generally towards the tube 72, resulting in a crimped attachment of the distal tip 20 to the tube 72 in the area of the crimp windows 36 as shown in FIG. 8. The distal tip 20 may be made from a wide variety of materials, known to those skilled in the art, which are capable of being deformed to take a crimp, either at room temperature or under elevated temperature. Such materials may include, but are not limited to metals, plastics, and alloys. The combination of the distal tip 20 with the tube 72 creates a suture securing tube device 76.

Figure 9:
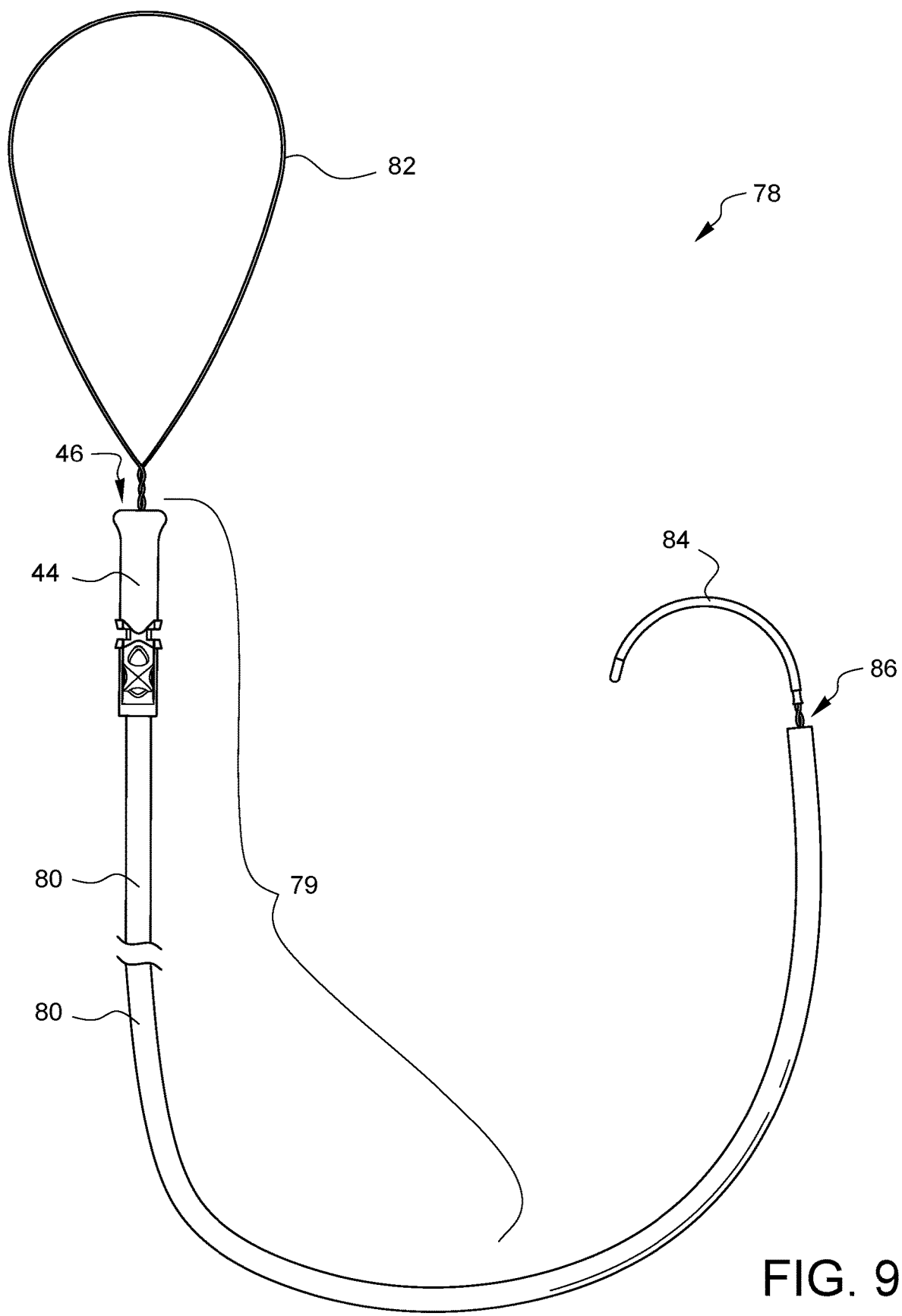
FIGS. 9-11 illustrate different assemblies that include another embodiment of a suture securing tube device.

FIG. 9 illustrates an assembly 78 that includes another embodiment of a suture securing tube device 79. This embodiment of the suture securing tube device 79 has a tube 80 with a distal tip 44 (like the distal tip 44 of FIG. 4A) crimped to its distal end. A snare loop 82 extends from the distal opening 46 and is coupled to a handle 84 exiting the proximal end 86 of the tube 80. Suture ends from a suture placed in or around tissue may be placed into the snare loop 82 and then the suture securing tube device 79 may be held while the handle 84 is pulled to draw the suture ends in through the distal opening 46, through the tube 80, and out the proximal end 86 of the tube 80. The suture ends exiting the proximal end 86 of the tube 80 may be clamped or otherwise secured, for example, by clamping the proximal end 86 of the tube 80 so the suture ends are pinched within the tube 80.

Figure 10:
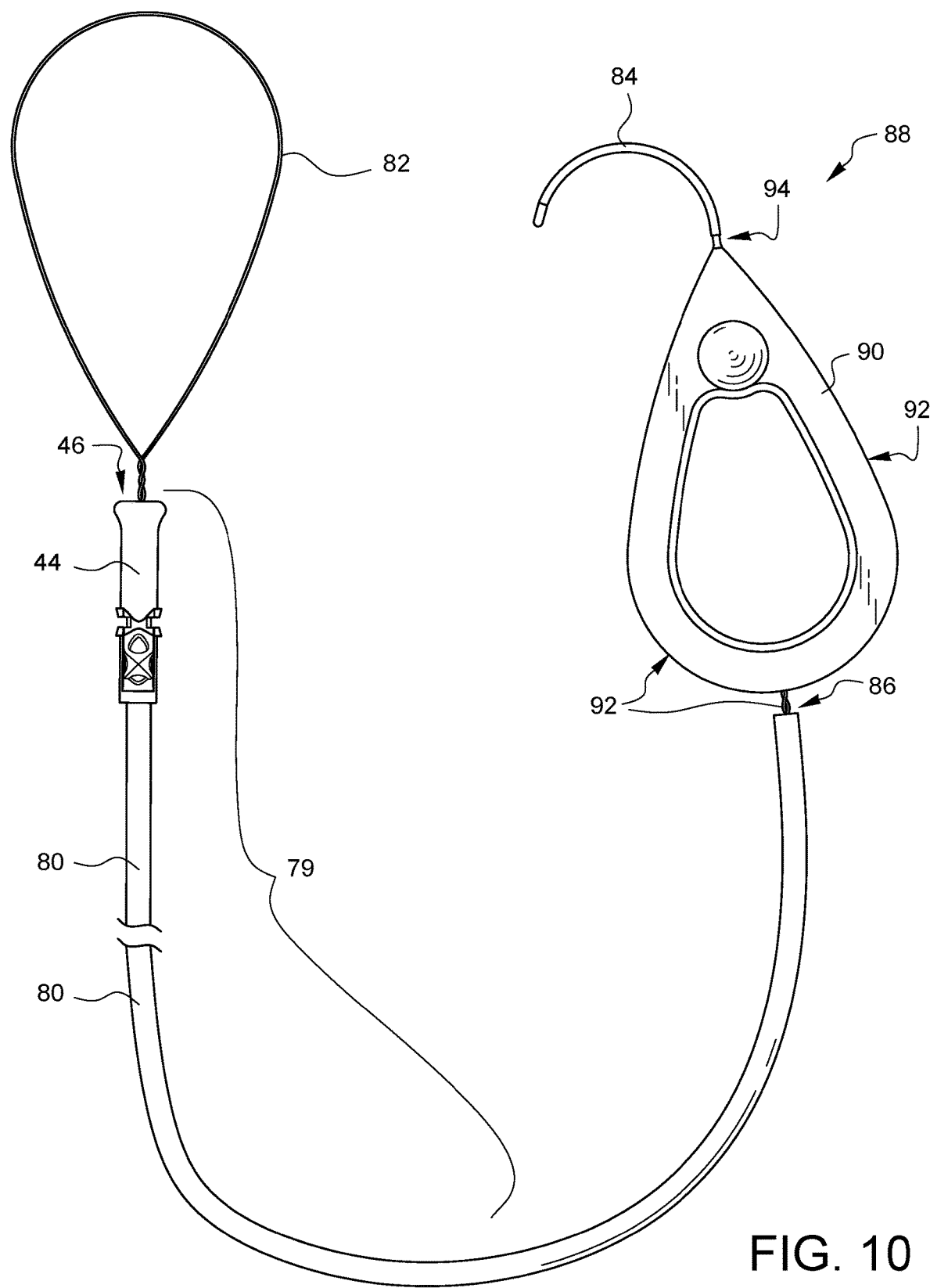

FIG. 10 illustrates an assembly 88 that includes another embodiment of a suture securing tube device 79. This embodiment of the suture securing tube device 79 has a tube 80 with a distal tip 44 (like the distal tip 44 of FIG. 4A) crimped to its distal end. A snare loop 82 extends from the distal opening 46 and is coupled to a handle 84 at the proximal end 86 of the tube 80. In this embodiment, however, the assembly 88 also includes a proximal target 90 around which the snare wires 92 pass before being joined to the handle 84 at location 94. The target 90 may make it easier to manipulate the handle end of the assembly 88 and/or can assist with packaging of the assembly 88. Although not illustrated, other embodiments may include a mechanical fastener at location 94 so that the proximal target 90 can be used to load the handle 84 into a mechanical fastening device that will secure the suture ends which will eventually be drawn therethrough. Suture ends from a suture placed in or around tissue may be placed into the snare loop 82 and then the suture securing tube device 79 may be held while the handle 84 is pulled to draw the suture ends in through the distal opening 46, through the tube 80, and out the proximal end 86 of the tube 80. The proximal target 90 can be removed prior to pulling the handle 84 or used as the handle. In embodiments where the handle is also used to load the suture through a mechanical knot, the target would need to be removed first. The suture ends exiting the proximal end 86 of the tube 80 may be clamped or otherwise secured, for example, by clamping the proximal end 86 of the tube 80 so the suture ends are pinched within the tube 80, or by fastening with a mechanical fastener that is large enough not to be pulled into the tube 80.

Figure 11:
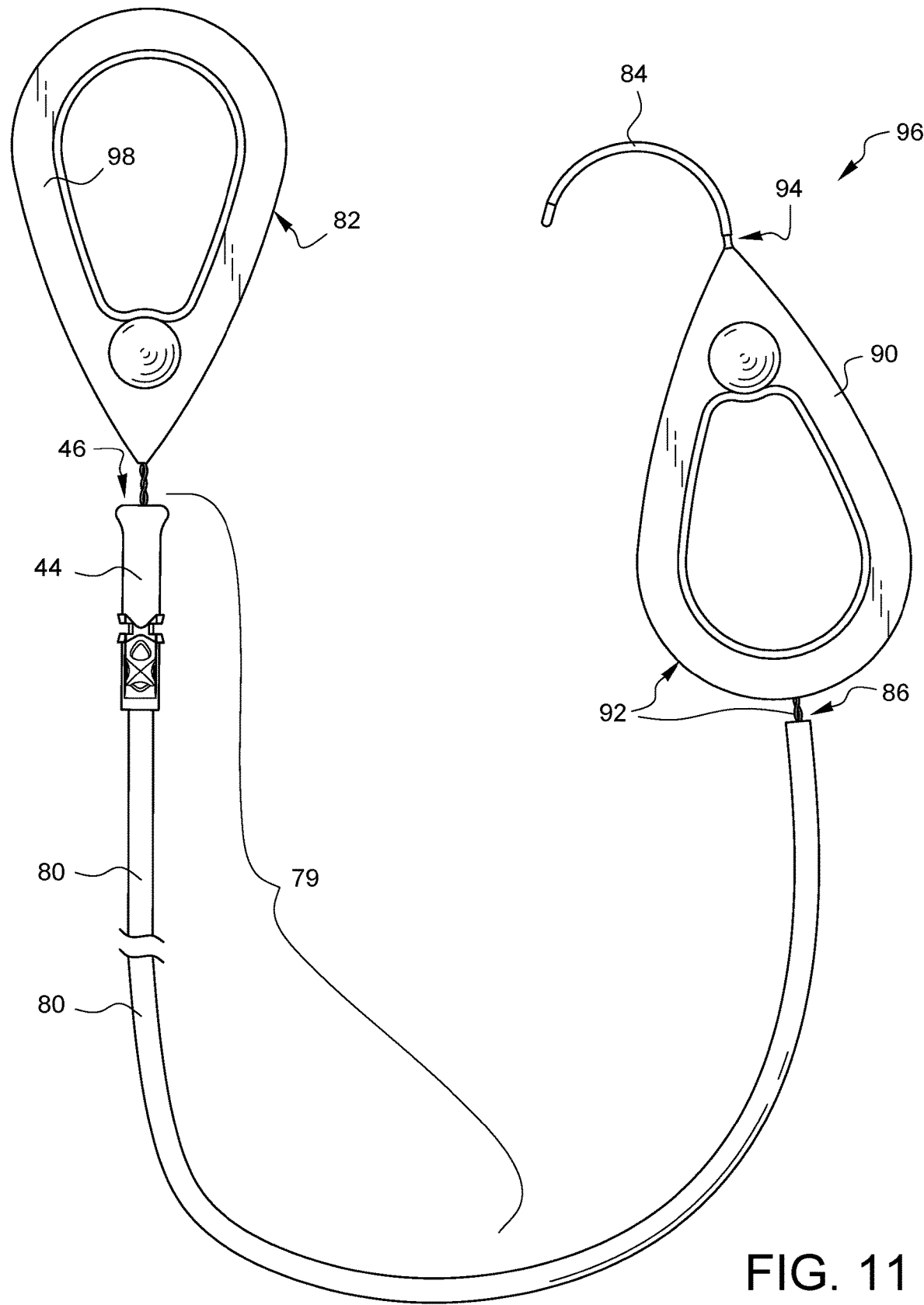

FIG. 11 illustrates an assembly 96 that is like the assembly 88 of FIG. 10 but also includes a removable distal target 98 inside the snare loop 82. The distal target 98 can facilitate packaging by maintaining the shape of the loop 82 prior to use. The distal target 98 can also help keep the loop 82 open while suture ends are placed therethrough. The target 98 would need to be removed prior to pulling the handle 84 to draw the suture ends through the suture securing tube device 79. Such a distal target 98 could also be used with embodiments like the assembly 78 of FIG. 9.

Figure 12:
FIGS. 12, 13A, and 13B are different views of another suture securing tube device.
Figure 13A:
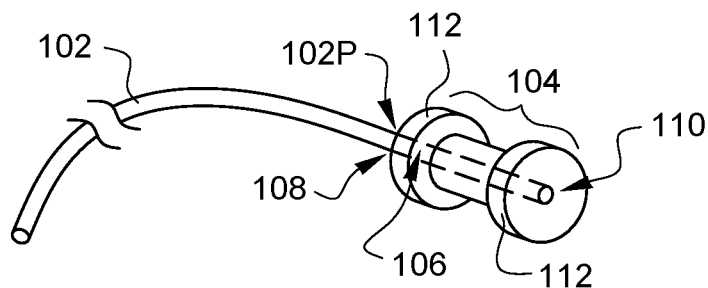
Figure 13B:
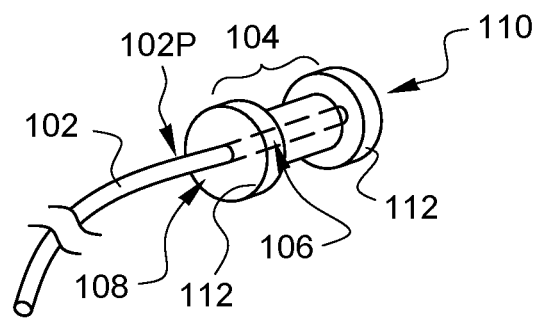

FIG. 12 illustrates another embodiment of a suture securing tube device 100. The embodied device 100 has a tube 102 which has a distal end 102D and a proximal end 102P. The proximal end 102 of the tube 100 is coupled to a flexible collar 104. FIGS. 13A and 13B show the flexible collar 104 from different perspectives. The flexible collar 104 defines a suture path 106 therein. The proximal end 102P of the tube 102 enters the suture path 106 on a first end 108 of the flexible collar 104. The suture path 106 exits the flexible collar 104 on a second end 110 of the flexible collar 104. Although the suture path 106 is shown as having a round cross-section in this embodiment, other embodiments could have cross-sections of one or more similar and/or different shapes. The cross-sectional shape of the tube 102 does not necessarily need to be congruent to the cross-sectional shape of the suture path 106.

The addition of the flexible collar 104 to the proximal end 102P of the tube 102 enables suture drawn therethrough to be pinched by the inside of the flexible collar 104 when squeezed by gripping, grasping, holding, or clamping device. It may be easier for the flexible collar 104 to grip suture when compressed, as opposed to being gripped directly by a medical instrument which is often hard, inflexible, and may have grooves which tend to prevent the proper grasping of suture. In this embodiment, the flexible collar 104 has side guides 112 which can help to keep a holding/clamping device from slipping off of the flexible collar 104. In this embodiment, the side guides 112 could be formed of a different material from the remainder of the flexible collar 104. Although the flexible collar 104 in this embodiment is shown as having a round cross-section, other embodiments could have cross-sections of one or more similar and/or different shapes. Additionally, the texture of the flexible collar can be smooth or rough. Similarly, the texture of the suture path may be smooth or rough.

Figure 14:
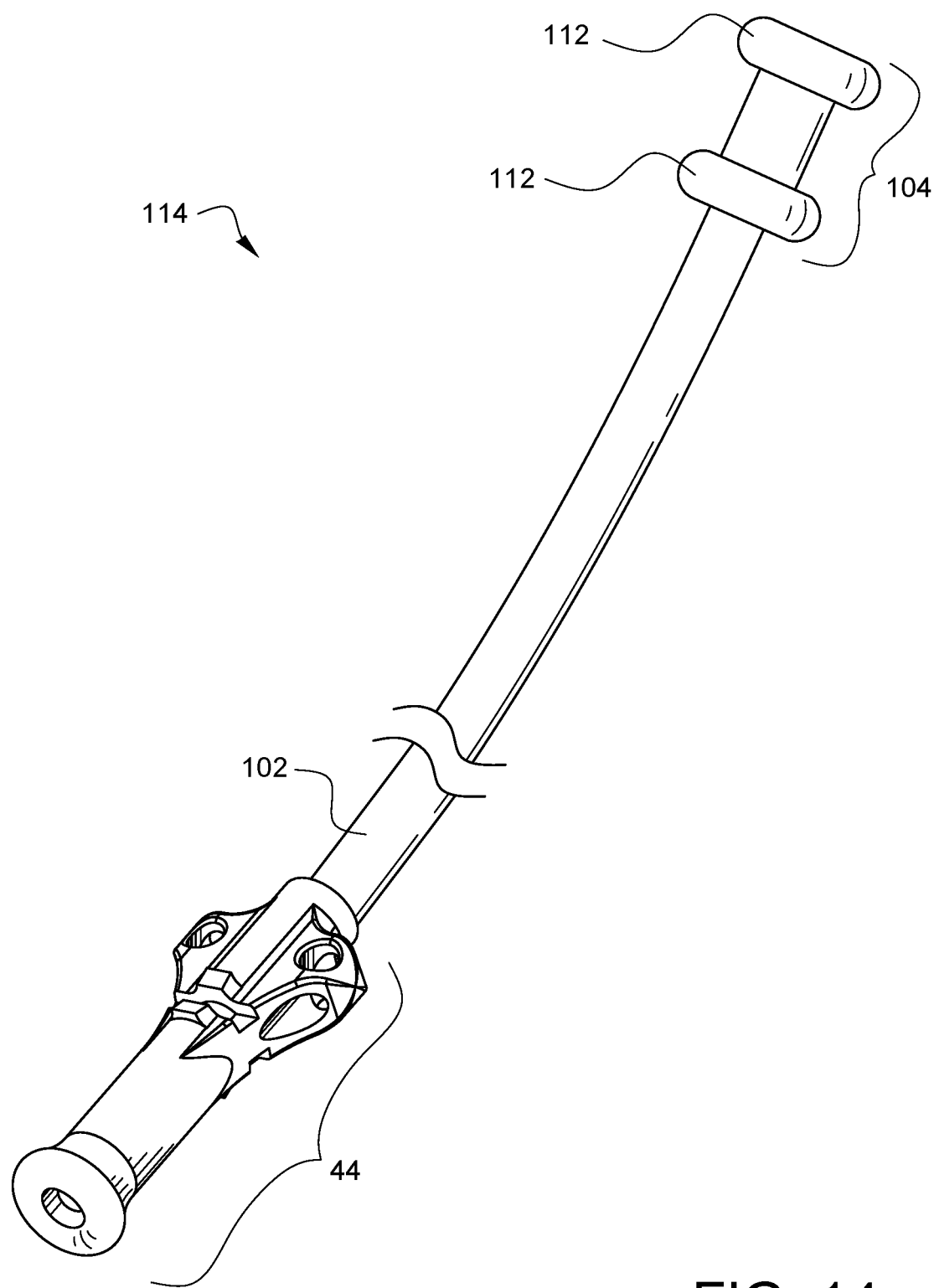
FIG. 14 illustrates a further embodiment of a suture securing tube device.

FIG. 14 illustrates another embodiment of a suture securing tube device 114. This device has a tube 102 with a flexible collar 104 and side guides 112 at the proximal end of the tube 102 as discussed with regard to the embodiment of FIGS. 13A-13B. The suture securing tube device 76 in FIG. 14, however, also has a distal tip 44 coupled to the distal end of the tube 102. The features of distal tip 44 have been discussed above with regard to FIGS. 4A and 4B, and the embodiment of FIG. 14 has the advantages of both the embodiments of FIGS. 4A and 13A.

Figure 15:
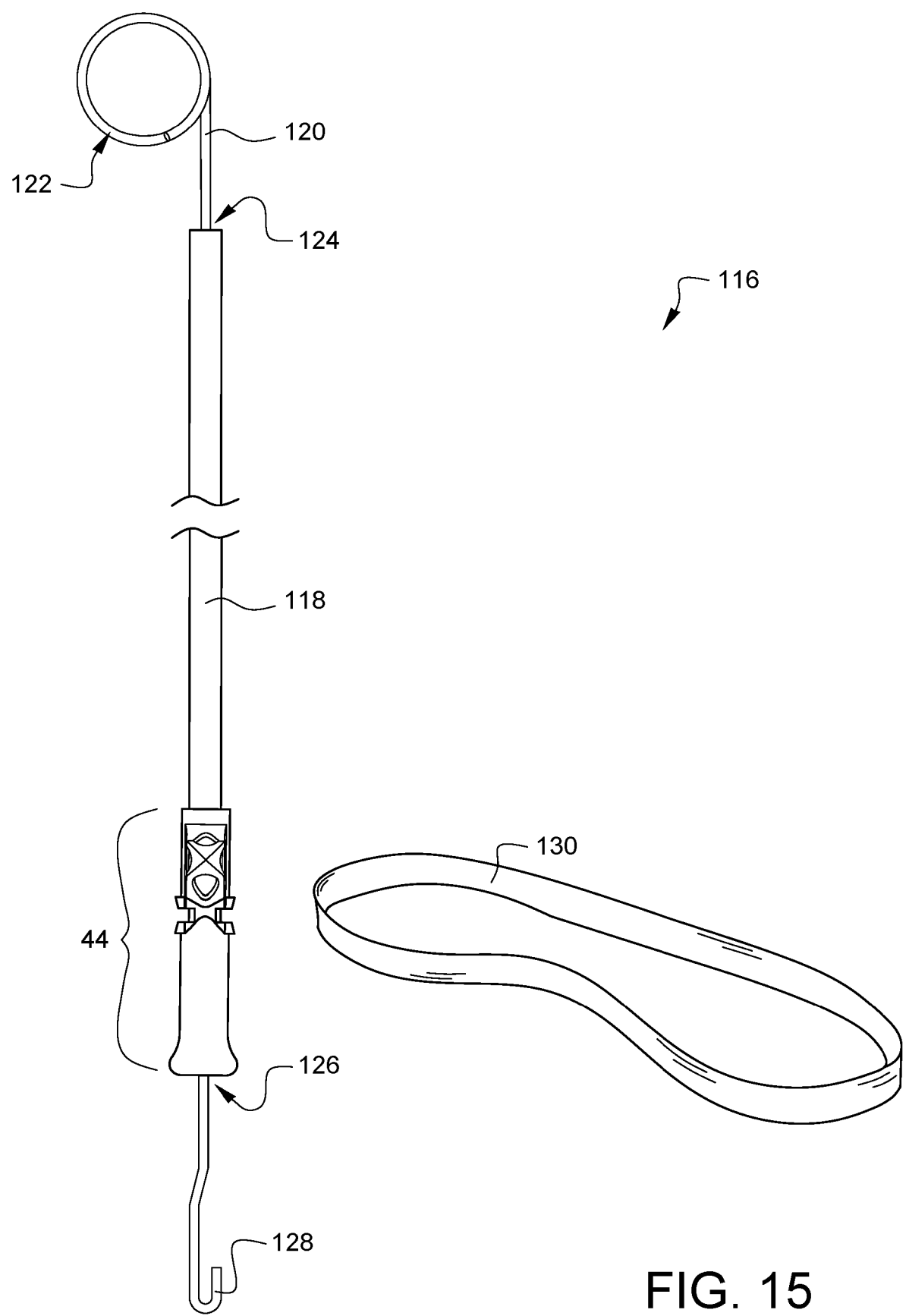
FIG. 15 illustrates another embodiment of a suture securing tube assembly.

FIG. 15 illustrates an assembly 116 that includes another embodiment of a suture securing tube device. This embodiment of the suture securing tube device has a tube 118 with a distal tip 44 (like the distal tip 44 of FIG. 4A) crimped to its distal end. A snare hook 128 extends from the distal opening 126 and is coupled to a handle 122 exiting the proximal end 124 of the tube 118. A band 130 (may be elastic or inelastic) is provided with this assembly 116. The band 130 may be wrapped around a vessel and opposite ends of the band 130 may be placed into the snare hook 128 and then the suture securing tube device may be held while the handle 122 is pulled to draw the ends of the band 130 in through the distal opening 126 and at least partway into the tube 118. This draws the band 130 tightly around the vessel creating a tourniquet, if desired. The wire 120 from which the handle 122 and the hook 128 are formed may be clamped or otherwise secured, for example, by clamping the proximal end 124 of the tube 118 so the suture ends are pinched within the tube 118.

Figure 16A:
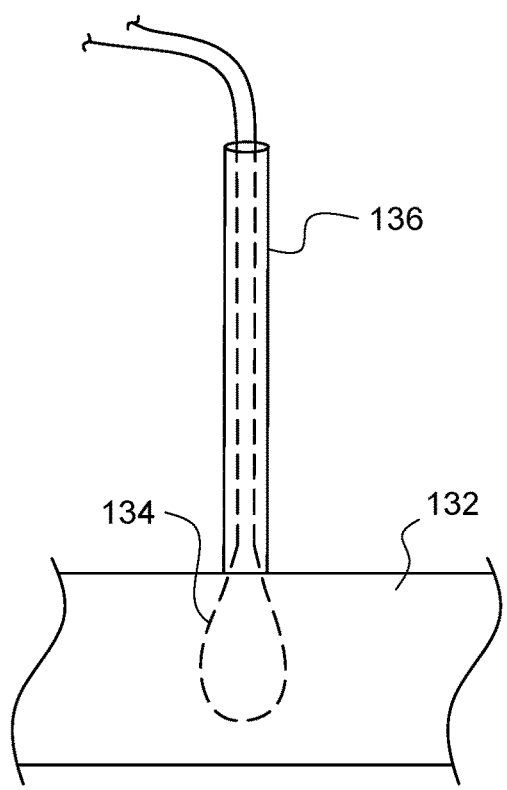
FIGS. 16A and 16B schematically illustrate a tissue through which a suture stitch has been placed and how a tube tourniquet can cut into the tissue when the suture is tensioned.
Figure 16B:
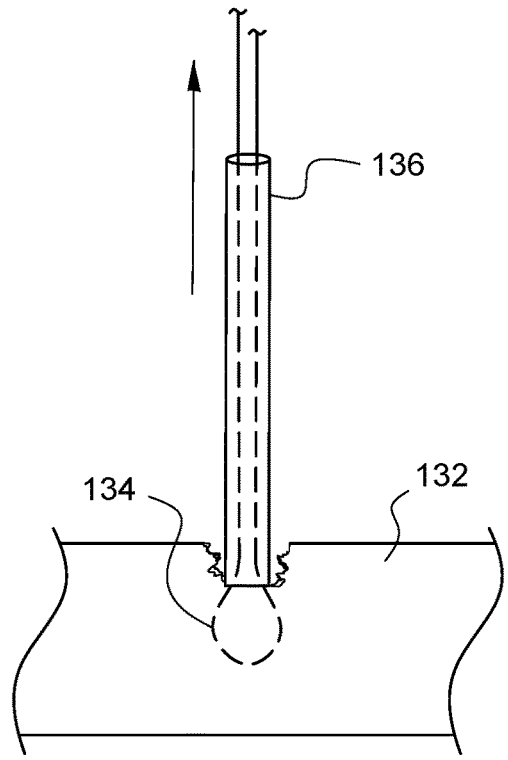

FIGS. 16A, 16B, 17A, and 17B schematically illustrate a tissue 132 through which a suture stitch 134 has been placed. In FIG. 16A, the ends of suture 134 have been snared through the tube 136, and the distal end of the tube 136 is in contact with the tissue 134. As illustrated in FIG. 16B, the suture ends are pulled, causing the suture tube 136 to press into and rip the tissue 132 because the force of the tube 136 against the tissue 132 is spread over such a thin profile of the tube 136. This type of tissue damage is highly undesirable.

Figure 17A:
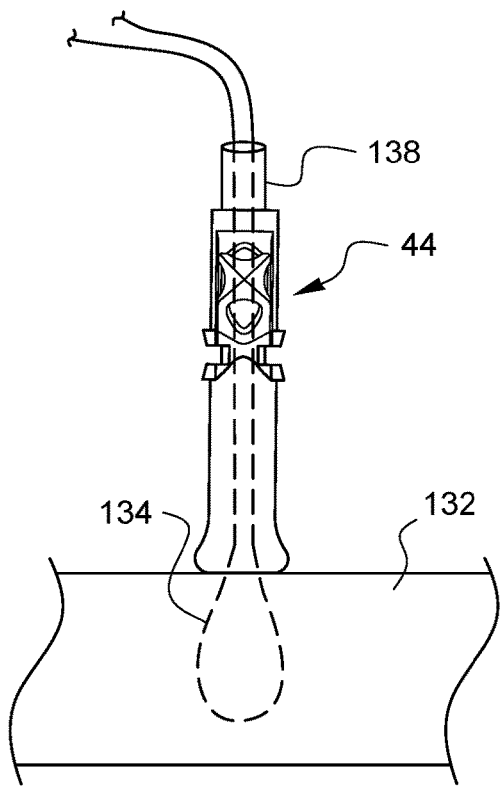
FIGS. 17A and 17B schematically illustrate a tissue through which a suture stitch has been placed and how an embodiment of a suture securing tube device can help prevent tissue damage.
Figure 17B:
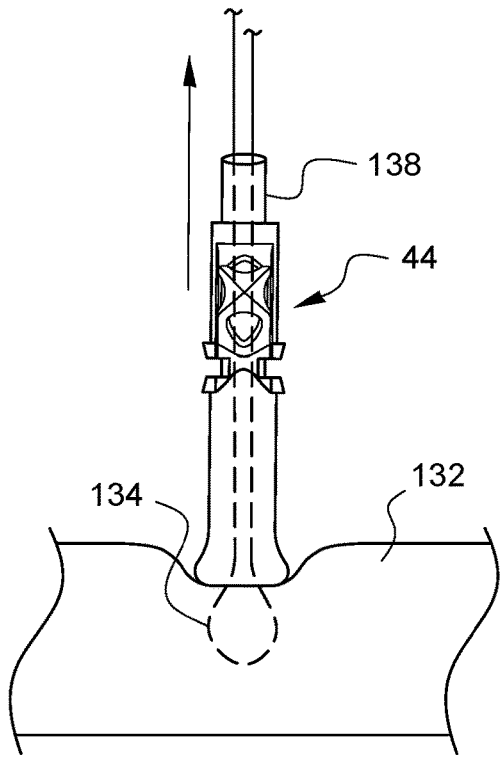

In FIG. 17A, the ends of suture 134 have been snared through a suture securing tube device having a tube 138 which is coupled to a distal tip 44. The flared end of the distal tip 44 (discussed previously) is in contact with the tissue 134. As illustrated in FIG. 17B, the suture ends are pulled the same way as with FIG. 16B, but in FIG. 17B, the less traumatic end of the distal tip 44 prevents ripping or tearing of the tissue. This provides a great advantage in surgical situations requiring a tourniquet style tube.

Figure 18A:
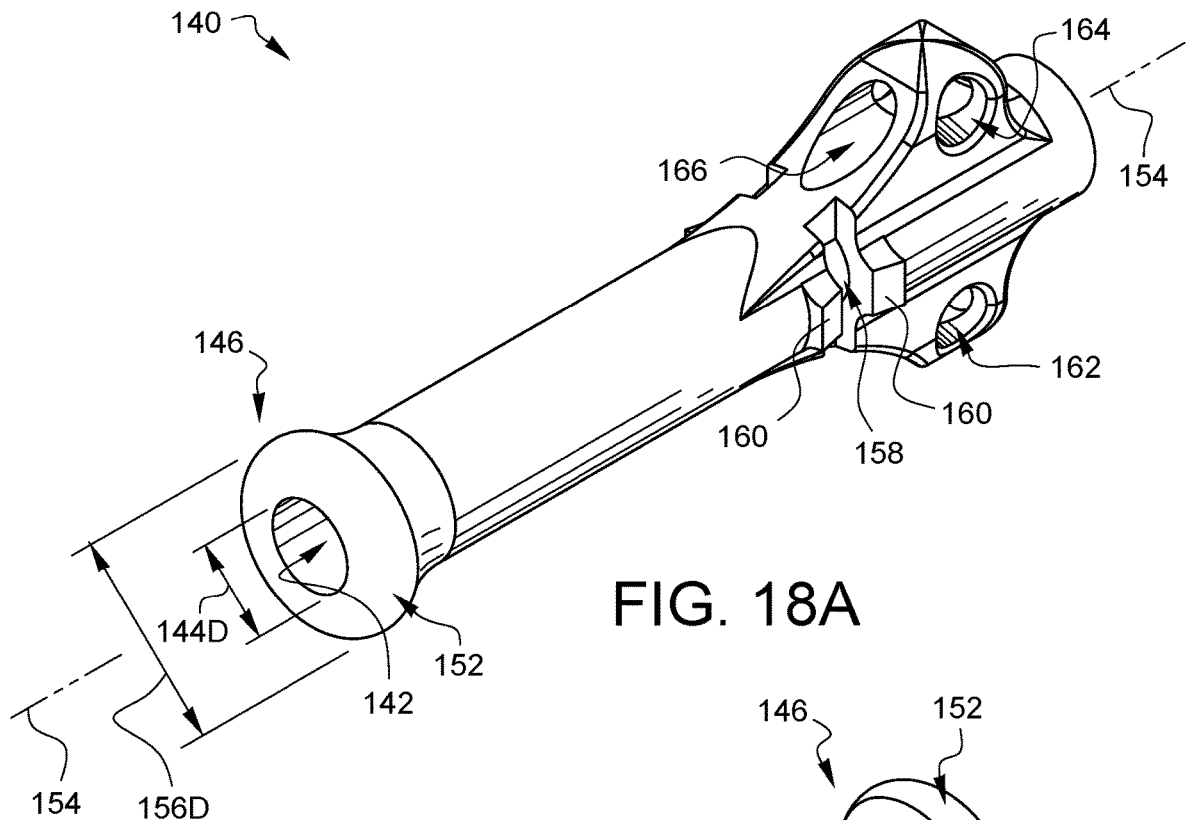
FIG. 18A is a perspective view of another embodiment of a distal tip, shown from a distal perspective.
Figure 18B:
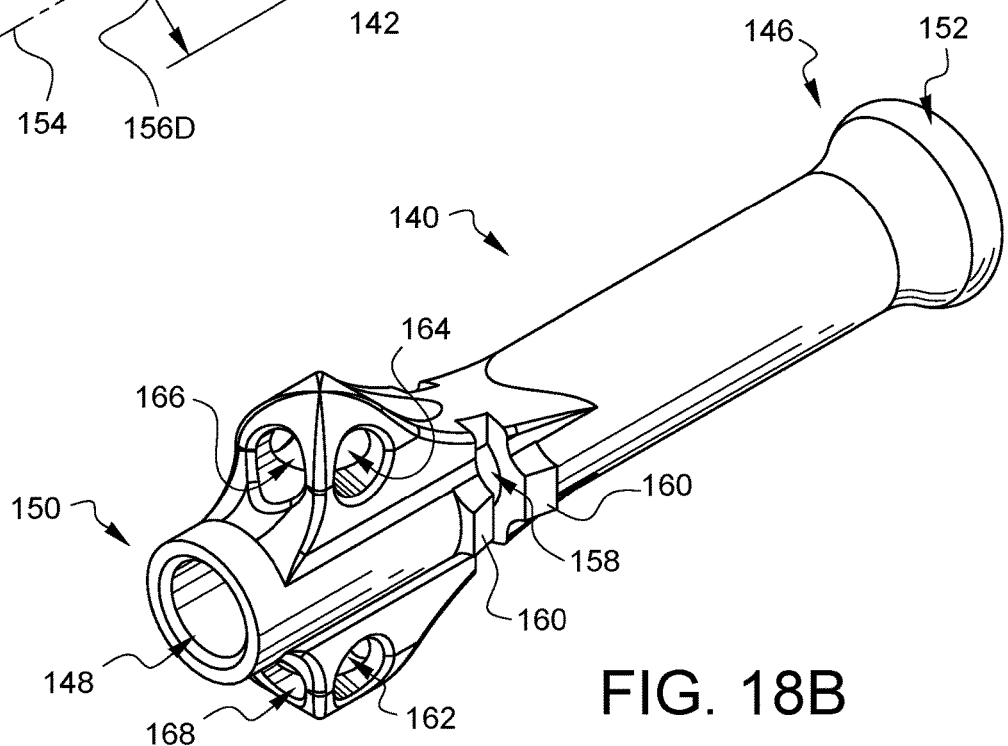
FIG. 18B is a perspective view of the distal tip of FIG. 18A, shown from a proximal perspective.

FIG. 18A is a perspective view of another embodiment of a distal tip 140, shown from a distal perspective, for a suture securing tube (not shown in this view). FIG. 18B is a perspective view of the distal tip 140 of FIG. 18A, shown from a proximal perspective. A distal opening 142 is located in the distal end 146 of the distal tip 140. In this embodiment, the distal opening 142 has a diameter 144D which is sized to accept a suture securing tube from another device, the advantages of which will be explained below. A tube interface opening 148 is located in the proximal end 150 of the distal tip 140. The distal tip 140 has a channel which communicates between the distal opening 142 and the tube interface opening 148. The distal end 146 of the distal tip 140 has a flared end 152 which has a radius configured to reduce tissue trauma when the distal end 146 of the distal tip 140 is pressed against tissue. As one example, the cross-sectional radius of the flared end 152 (taken on a plane in which the longitudinal axis 154 of the distal tip 140 lies) is larger than the cross-sectional radius of the tube edges of the tube (not visible in this view) which will be mated with the tube interface opening 148. As another example, the diameter 156D of the flared end 152 may be larger than the diameter of the tube (not visible in this view) which will be mated with the tube interface opening 148. Other embodiments may have other definitions of how the flaring of the flared end 152 reduces tissue trauma vs a simple tube, and, as noted with the previous embodiment, the definition of the flared end 152 does not need to be determined based on a comparison with the tube (not visible in this view).

The distal tip 140 also has crimp windows 158 located between crimp directors 160. As will be discussed in more detail later in this specification, when pressure is applied to the crimp directors 160, the inner edges of the crimp window 158 will pinch into a tube (not shown in this view), that has been placed in the tube interface opening 148, in order to secure the tube to the distal tip 140. Other embodiments might not have one or more crimp windows and/or one or more crimp directors, as the tube (not shown in this view) could be secured by other methods, including, but not limited to ultrasonic welding, gluing, press fitting, shrinking, melting, or threading. Still other embodiments might not have one or more crimp windows and/or one or more crimp directors because the tube (not shown in this view) could be formed continuously with the distal tip.

This embodiment of the distal tip 140 also defines four anchor channels 162, 164, 166, and 168 through which one or more tie-down sutures (not shown) may be passed to hold the distal tip 140 in a particular orientation during a surgery in order to help keep a surgical field organized. For example, if the distal tip 140 of a suture securing tube is used in conjunction with a purse string suture that is cinched against a cannula placed in an aorta during cardio-pulmonary bypass, a separate suture may be routed through the anchor channels 162, 164 of the distal tip 140 and secured around the cannula to keep the distal tip 140 and the tube (not shown in this view) in line with the cannula rather than allowing the distal tip 140 to flop away from the cannula. In the embodiment of FIGS. 18A and 18B, the anchor channels 162, 164 face a direction that is not parallel to the longitudinal axis 154 of the distal tip 140. This embodiment also has anchor channels 166, 168 which face a direction that is substantially parallel to the longitudinal axis 154. These channels 166, 168 provide other anchoring options. Furthermore, in this embodiment, anchor channel 162 intersects anchor channel 168. Similarly, anchor channel 164 intersects anchor channel 166, enabling sutures routed into one anchor channel to be routed out of an intersecting channel, providing surgeons with even more options and flexibility for anchoring purposes. Other embodiments may have different numbers of anchor channels or no anchor channels at all. Other embodiments may have one or more anchor channels which face in a different direction as compared to the anchor channels 162, 164, 166, and 168 of FIGS. 18A and 18B.

Figure 19:
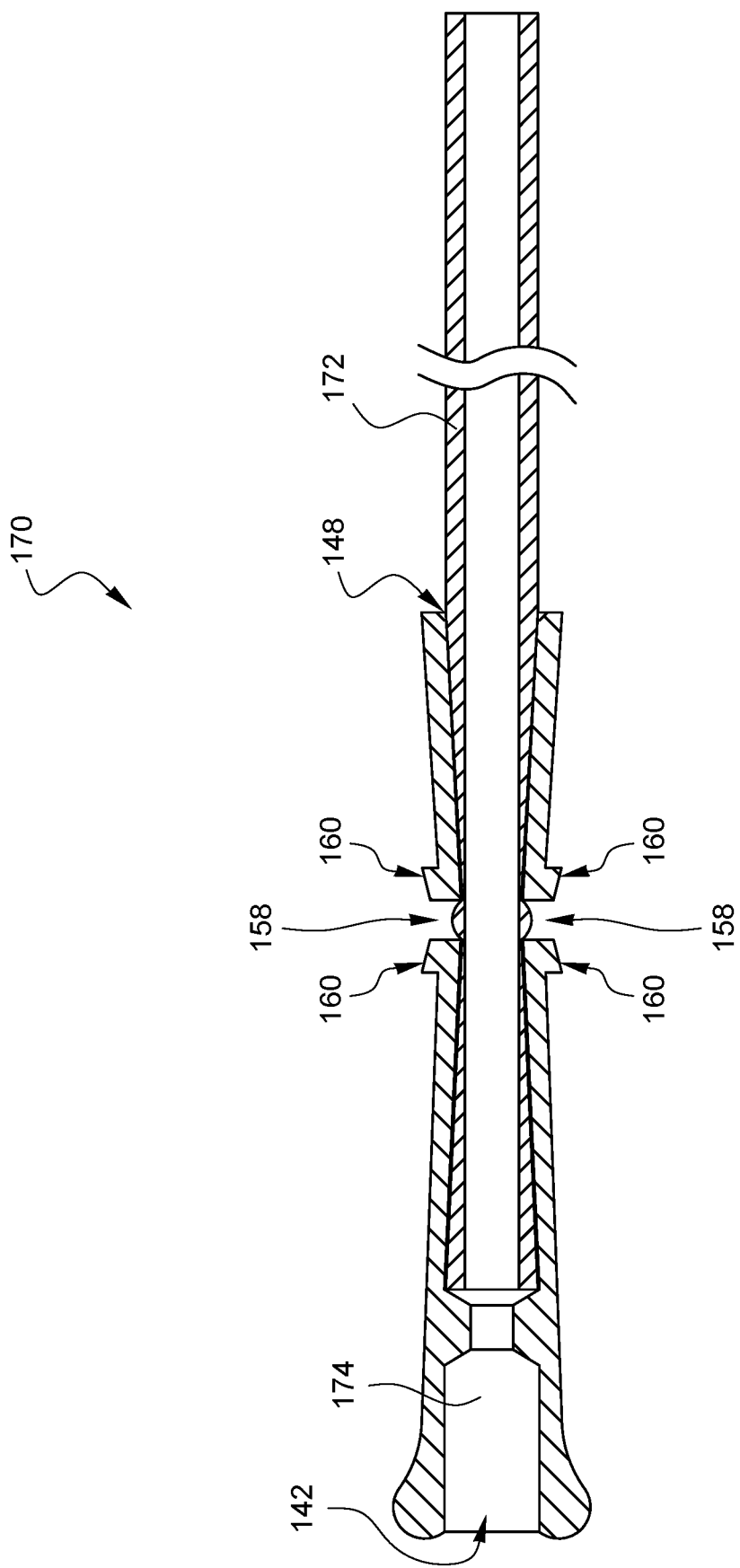
FIG. 19 is a side cross-sectional view schematically illustrating one example of the distal tip of FIG. 18A crimped onto a tube to form a suture securing tube device.

FIG. 19 is a side cross-sectional view schematically illustrating one example of the distal tip 140 of FIG. 18A crimped onto a tube 172 to form a suture securing tube device 170. As shown in FIG. 19, and similar to previous embodiments, a proximal end of the tube 172 has been inserted into the tube interface opening 148 of the distal tip past the crimp windows 158. As shown in FIG. 19, the crimp directors 160 have been crimped to force the edges of the crimp window 158 into the tube 172, thereby securing the distal tip to the tube 172. In this cross-sectional view, the distal opening 142 can be seen, and it differs from previous distal openings in that it communicates with a second tube interface opening 174. The second tube interface opening 174 of this embodiment enables multiple suture securing tube assemblies to be stacked if a longer tube assembly is needed.

Figure 20A:
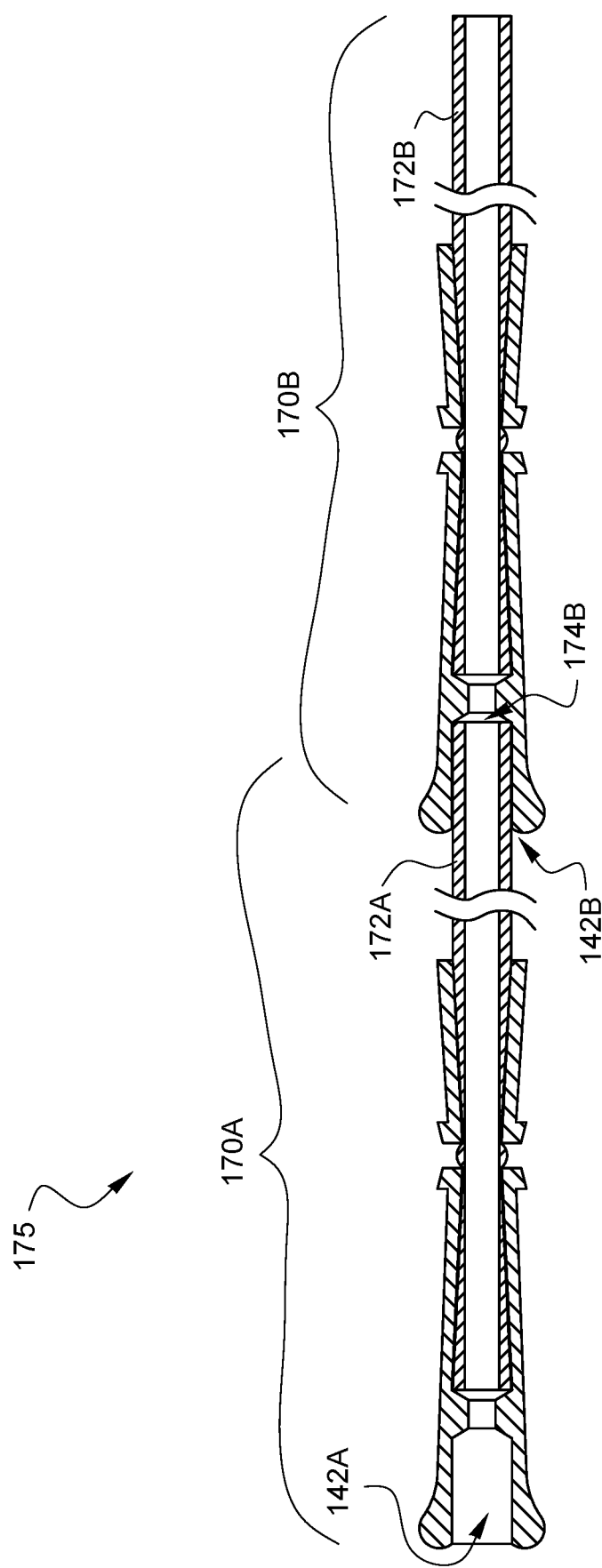
FIG. 20A illustrates, in a side cross-sectional view, two suture securing tube devices of FIG. 19 coupled together to make a larger suture securing tube device.

FIG. 20A illustrates two suture securing tube devices 170A and 170B (which each are like the suture securing tube device 170 of FIG. 19, but with an "A" or a "B" suffix to denote their similar elements). The tube 172A of tube device 170A has been inserted into the second tube interface opening 174B of tube device 170B. Together, the stacked tube devices 170A, 170B make a longer tube device 175 having a distal opening 142A and a proximal tube 172B.

Figure 20B:
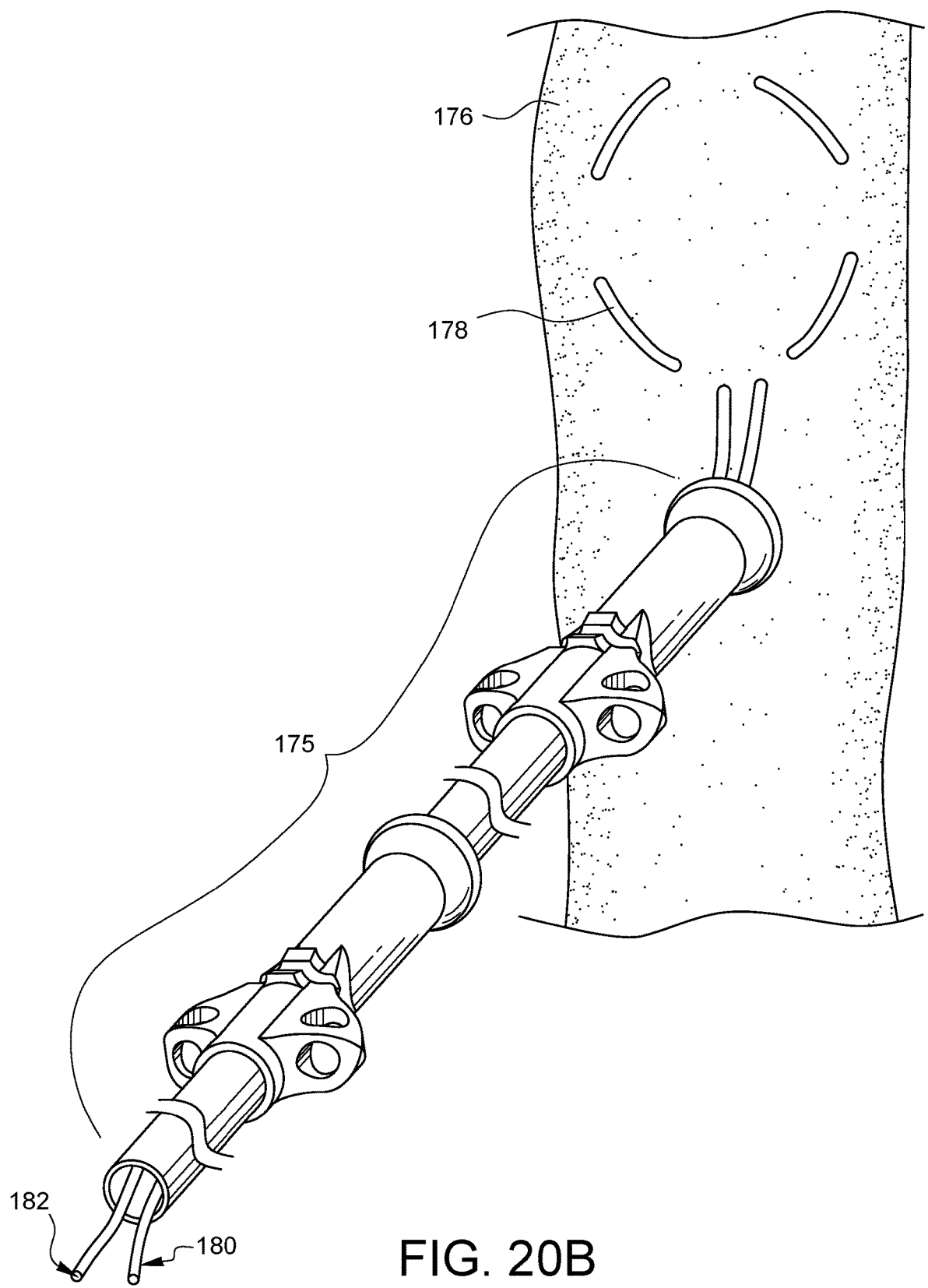
FIG. 20B is a perspective view of the stacked suturing devices of FIG. 20A.

FIG. 20B illustrates a tissue 176 in which a suture 178 has been stitched. The longer tube device 175 from FIG. 20A is shown in a perspective view, and the suture ends 180, 182 of the suture 178 have been snared through the distal opening and have exited the proximal tube. As the suture ends 180, 182 are tensioned, it is believed that the distal suture tube will stay aligned within the proximal device tip opening, thereby maintaining the integrity of the longer tube device 175 and allowing the suture ends 180, 182 to be clamped when a desired tension is reached.

Figure 21:
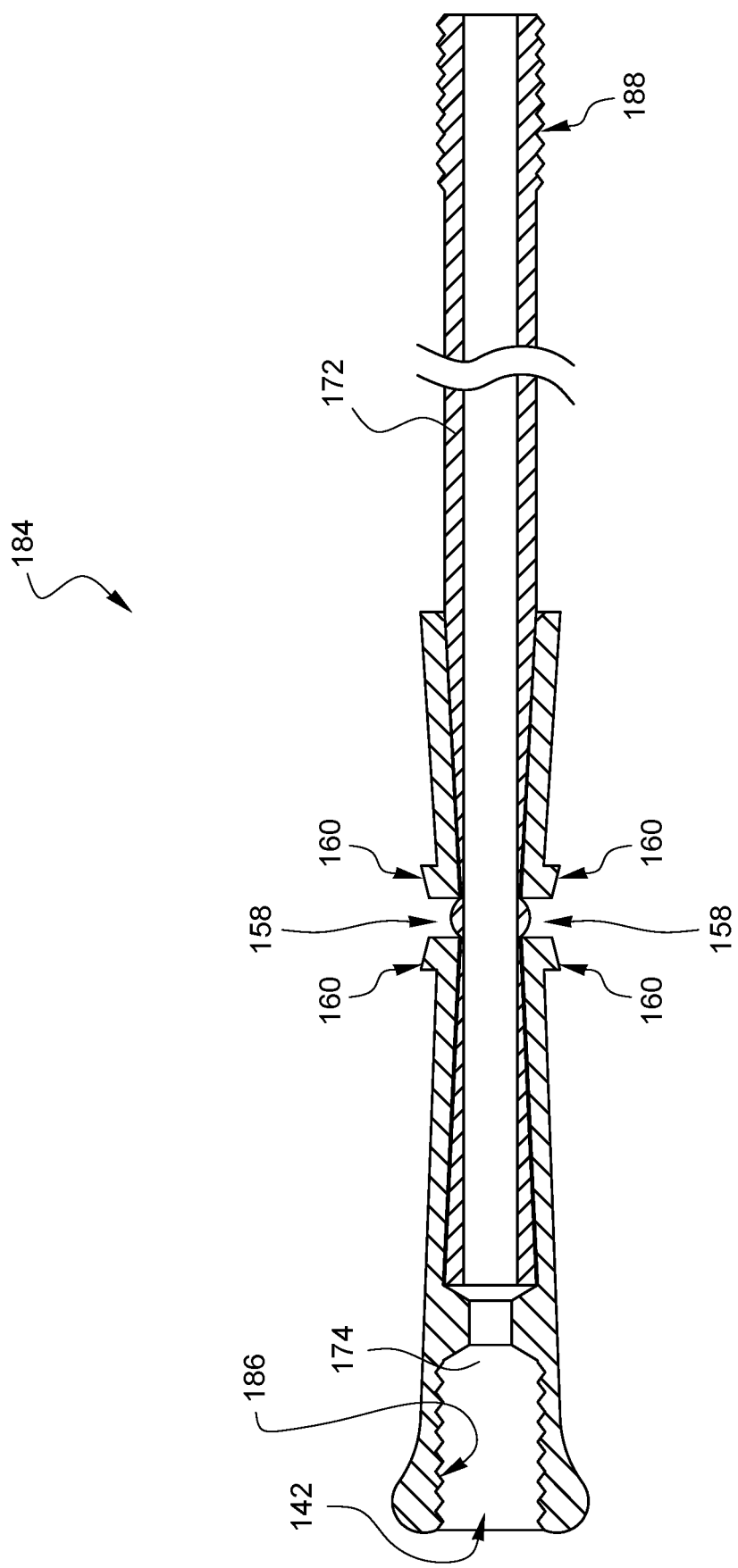
FIG. 21 illustrates another embodiment of a suture securing tube device, which is like the embodiment of FIG. 19, with the addition of features which will enable it to have a more positive connection between stacked devices.

FIG. 21 illustrates another embodiment of a suture securing tube device 184, which is like the embodiment of FIG. 19 discussed above, with the addition of features which will enable it to have a more positive connection between stacked devices. In the embodiment of FIG. 21, the proximal end of the tube 172 has threads 188 on its outer surface. The device 184 also has corresponding threads 186 on the inner surface of the second tube interface opening 174. The device 184 is capable of being used on its own as a suture securing tube device, however, multiple devices 184 may be joined together by threading the threaded tube 188 of one device into the threaded second tube interface opening 174 of another device.

Figure 22:
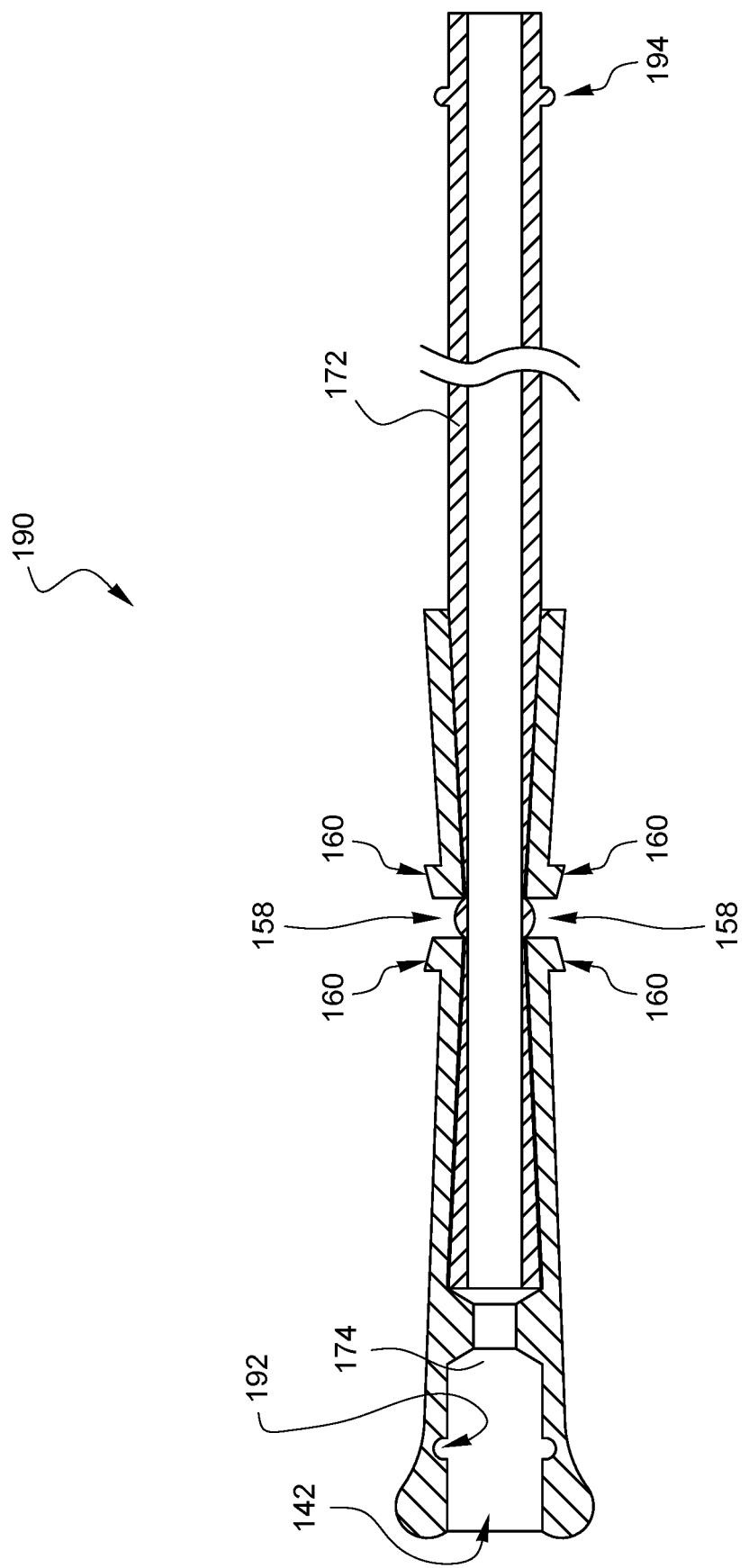
FIG. 22 illustrates another embodiment of a suture securing tube device, which is like the embodiment of FIG. 19, with the addition of different features which will enable it to have a more positive connection between stacked devices.

FIG. 22 illustrates another embodiment of a suture securing tube device 190, which is like the embodiment of FIG. 19 discussed above, with the addition of alternate features which will enable it to have a more positive connection between stacked devices. In the embodiment of FIG. 22, the proximal end of the tube 172 has a protrusion 194 on its outer surface. The device 190 also has a corresponding detent 192 on the inner surface of the second tube interface opening 174. The device 190 is capable of being used on its own as a suture securing tube device, however, multiple devices 190 may be joined together by pressing the tube 172 of one device into the second tube interface opening 174 of another device so that the protrusion 194 of the one device engages the detent 192 of the other device. Both the threaded features of the embodiment of FIG. 21 (as one example) and the protrusion/detent features of FIG. 22 (as another example) are examples of securing interface features that comprise a pair of corresponding securing interface features. For example, the male/female threads are one pair of corresponding securing interface features, and the protrusion/detent features are another pair of corresponding securing interface features. Other types of corresponding securing interface features will be apparent to those skilled in the art upon reading the above description.

Figure 23A:
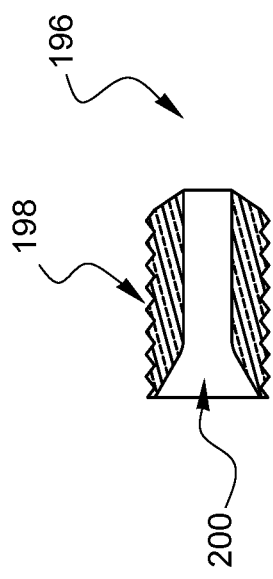
FIG. 23A illustrates a cross-sectional view of one embodiment of a distal plug for the device of FIG. 21.
Figure 23B:
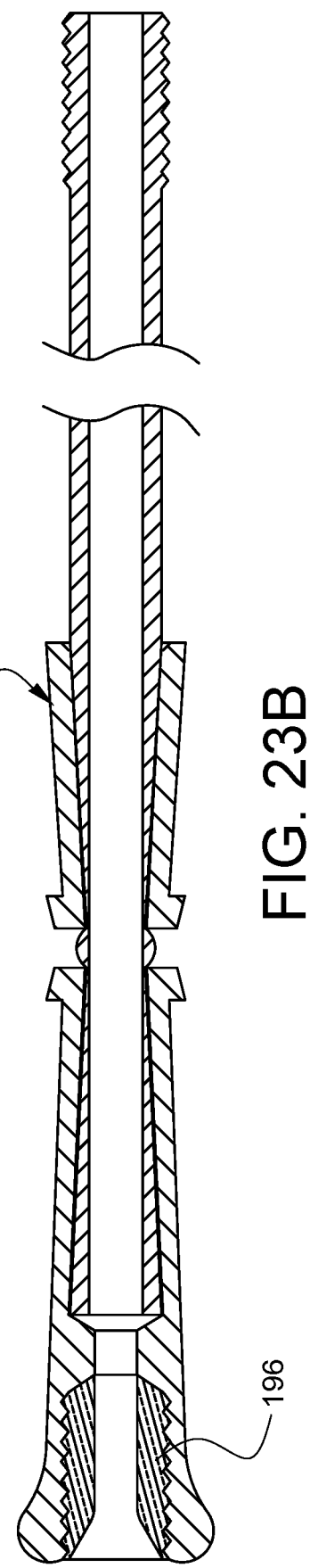
FIG. 23B illustrates a cross-sectional view of the distal plug of FIG. 23A installed in the device of FIG. 21.

In many cases, it should be suitable for embodiments of the suture securing tube devices of FIGS. 21 and 22 to be used directly with suture without concern that the threads or the detents in the second suture interface opening will cut into or snag any suture which is drawn therethrough. However, in some cases, it may be desirable to supply a distal plug 196, as illustrated in cross-sectional view in FIG. 23A for the device of FIG. 21. If the device will not be used in a stacked group, then the distal plug 196 has threads 198 which correspond to the threads 186 in the second tube interface opening 174 of device 184. The distal plug 196 also has a smooth inner channel 200 which can provide a smooth suture passage when the distal plug is threaded into the device 184 as illustrated in FIG. 23B.

Figure 24A:
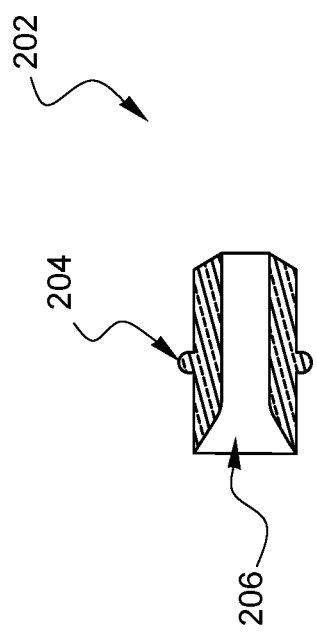
FIG. 24A illustrates a cross-sectional view of one embodiment of a distal plug for the device of FIG. 22.
Figure 24B:
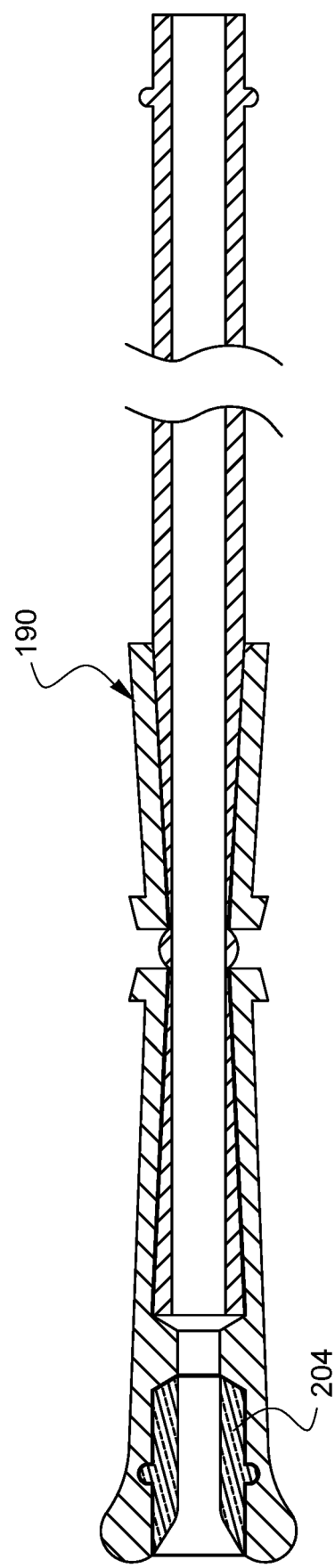
FIG. 24B illustrates a cross-sectional view of the distal plug of FIG. 24A installed in the device of FIG. 22.

Similarly, as illustrated in the cross-sectional view of FIG. 24A, another embodiment of a distal plug 202 may be supplied for the device of FIG. 22. If the device will not be used in a stacked group, then the distal plug 202 has protrusions 204 which correspond to the detents 192 in the second tube interface opening 174 of device 190. The distal plug 202 also has a smooth inner channel 206 which can provide a smooth suture passage when the distal plug is engaged into the device 190 as illustrated in FIG. 24B.

Figure 25A:
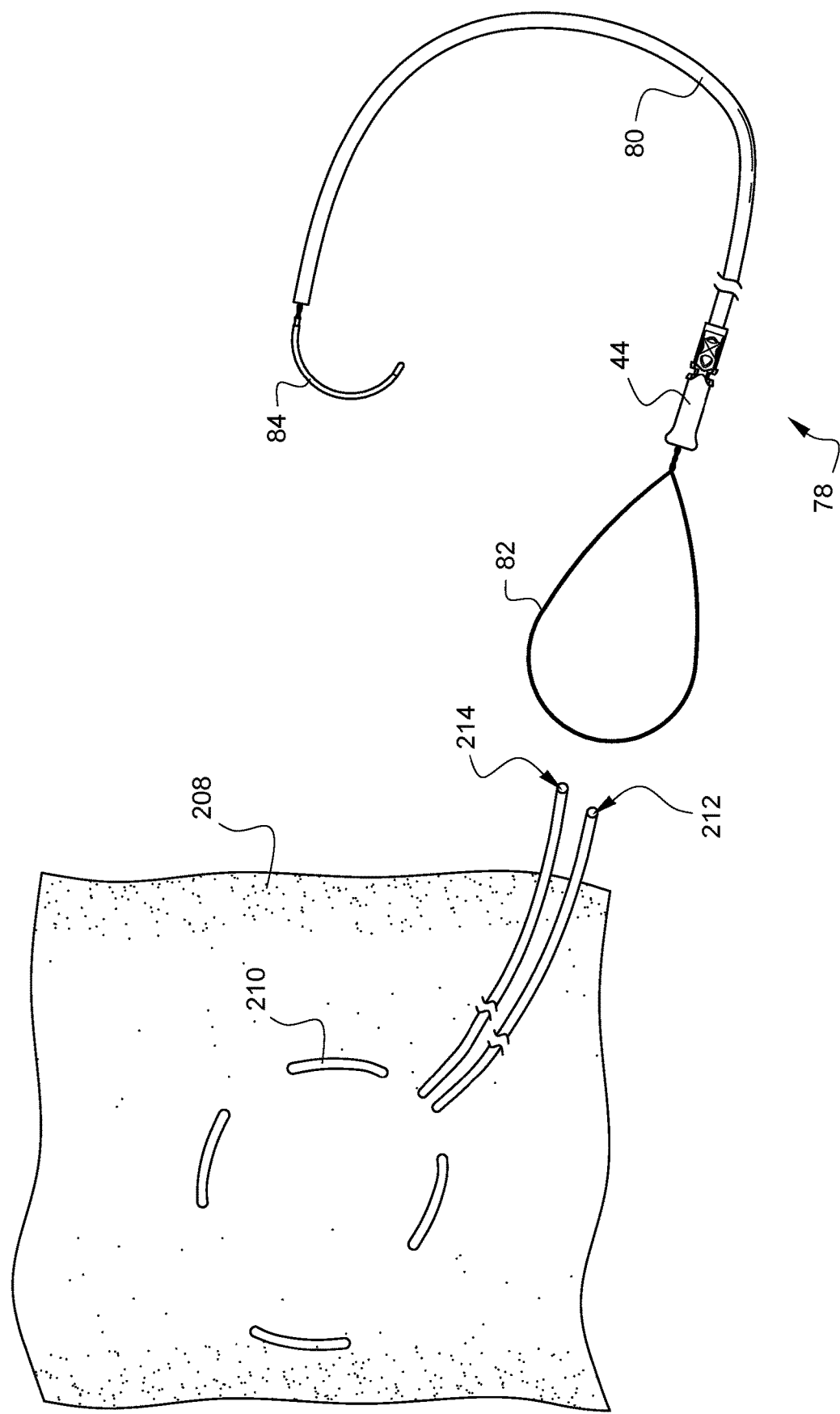
FIGS. 25A-25G illustrate a method of cannulation using the assembly of FIG. 9.
Figure 25B:
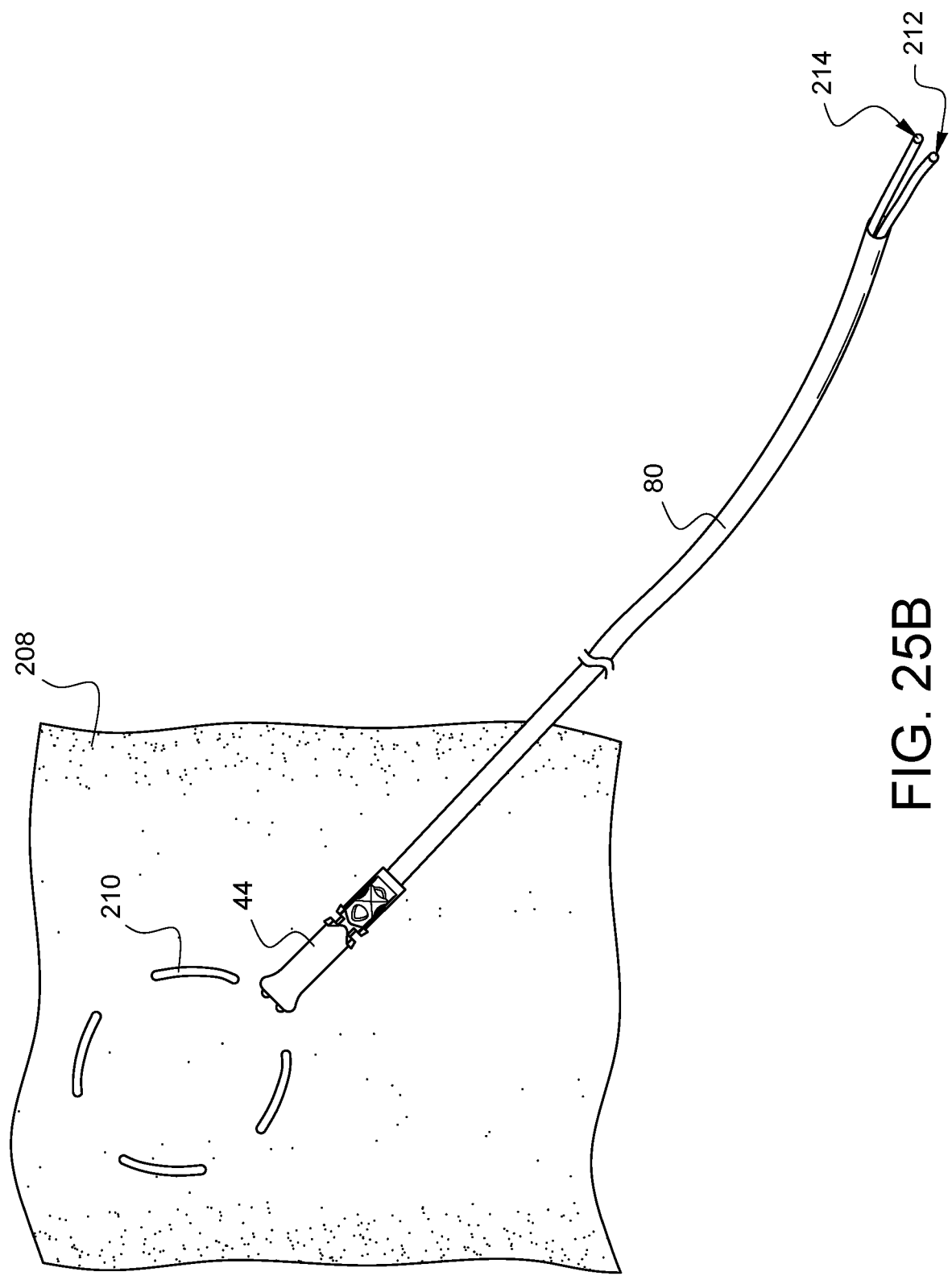
Figure 25C:
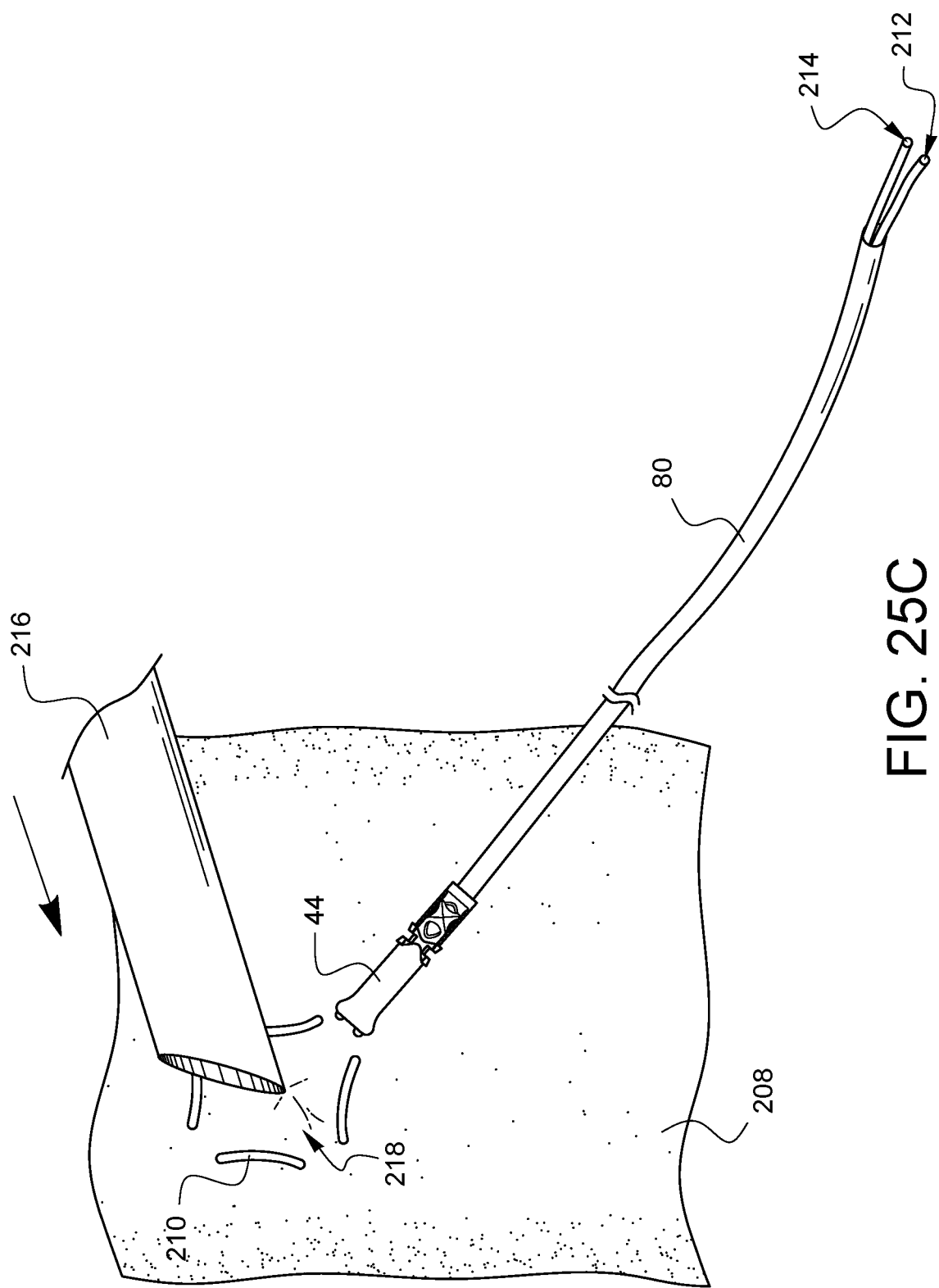
Figure 25D:
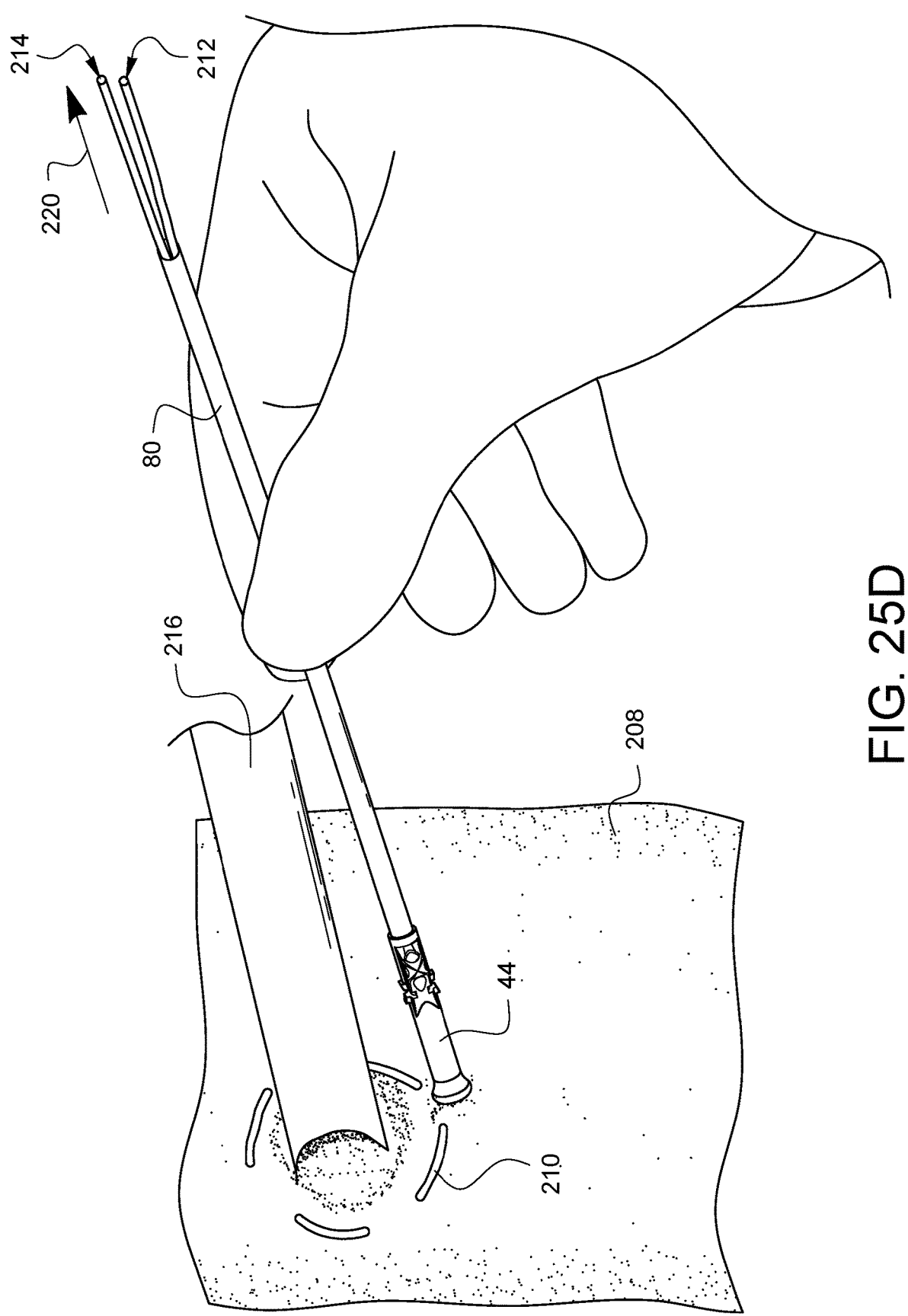
Figure 25E:
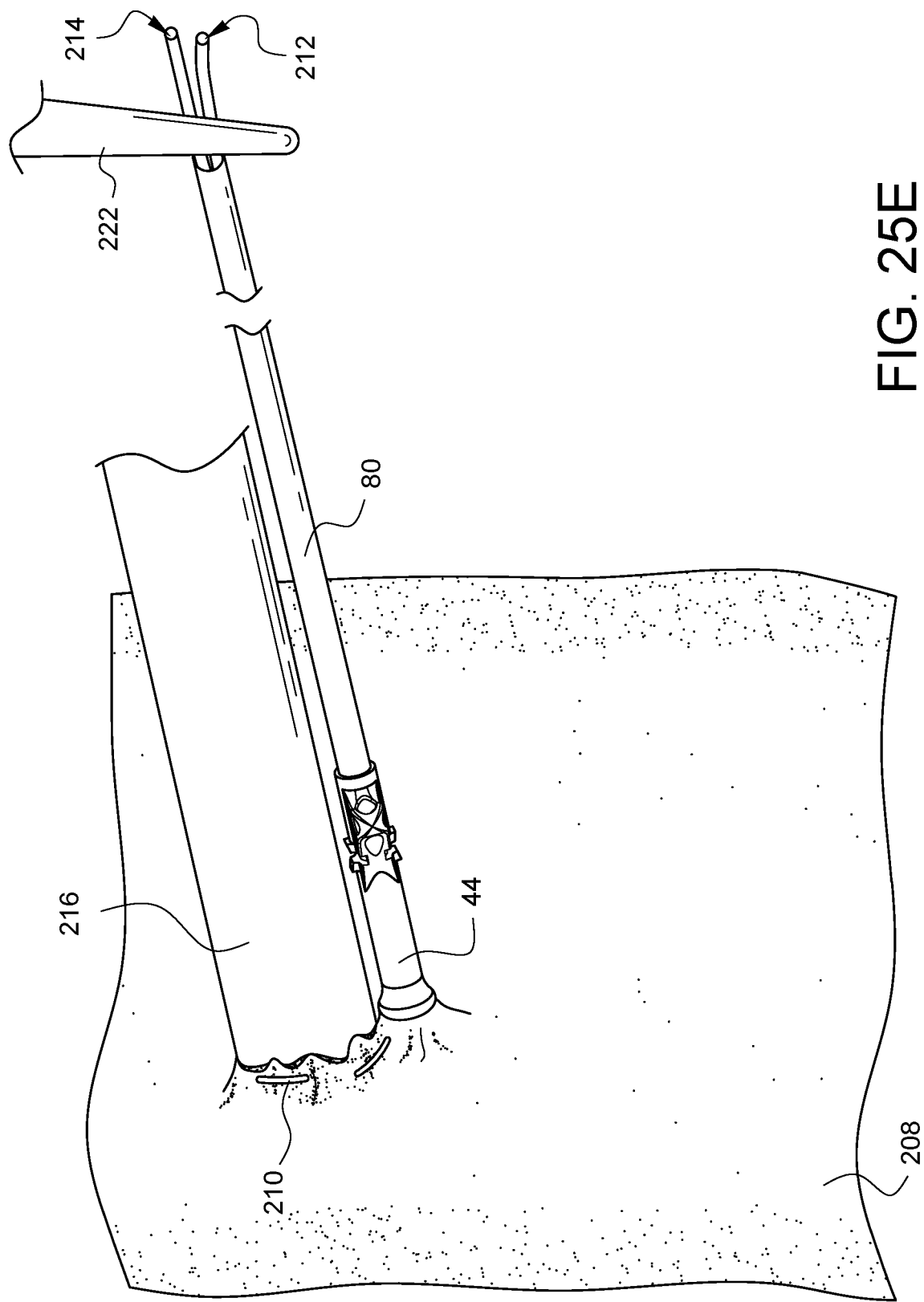
Figure 25F:
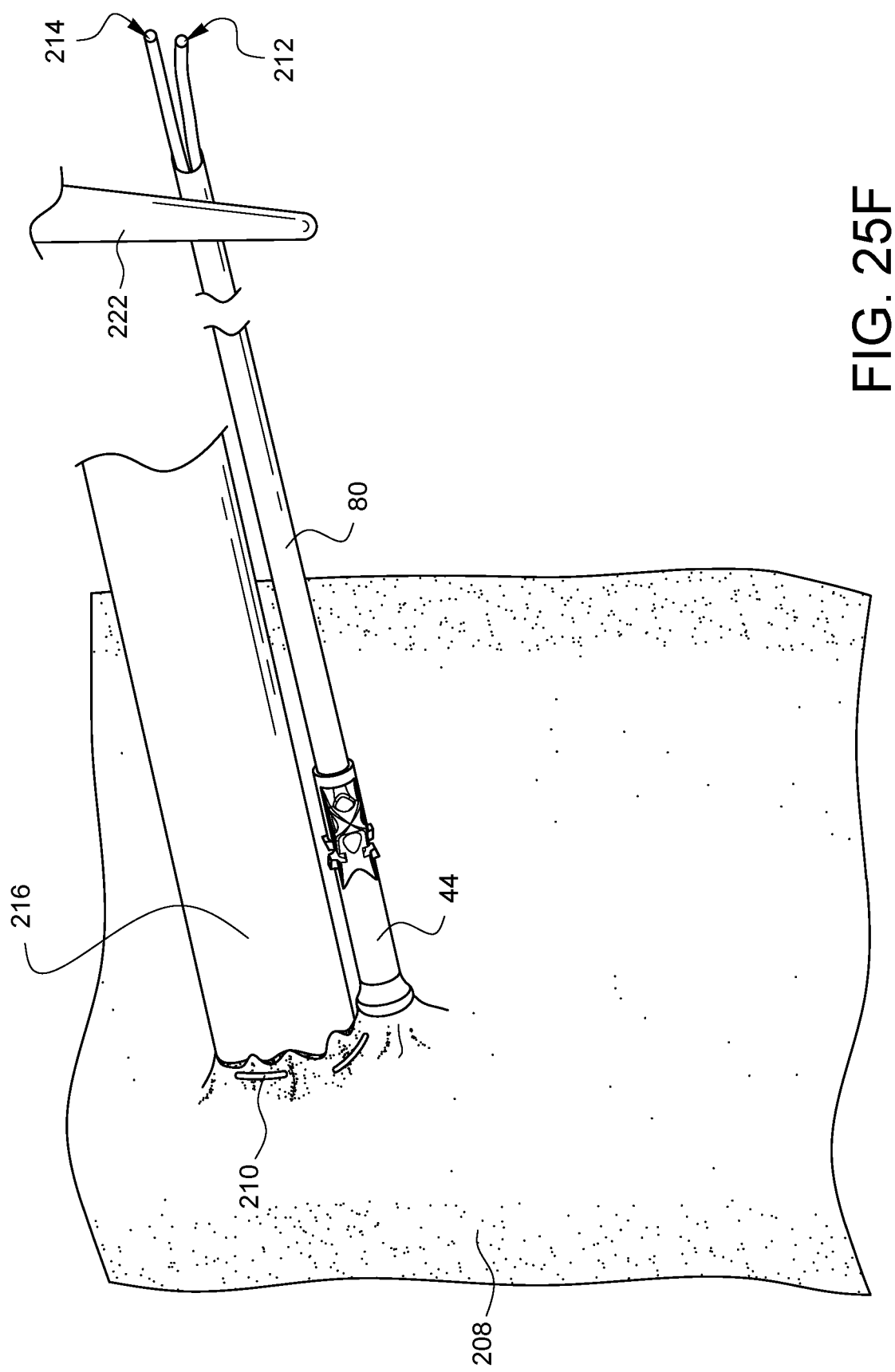
Figure 25G:
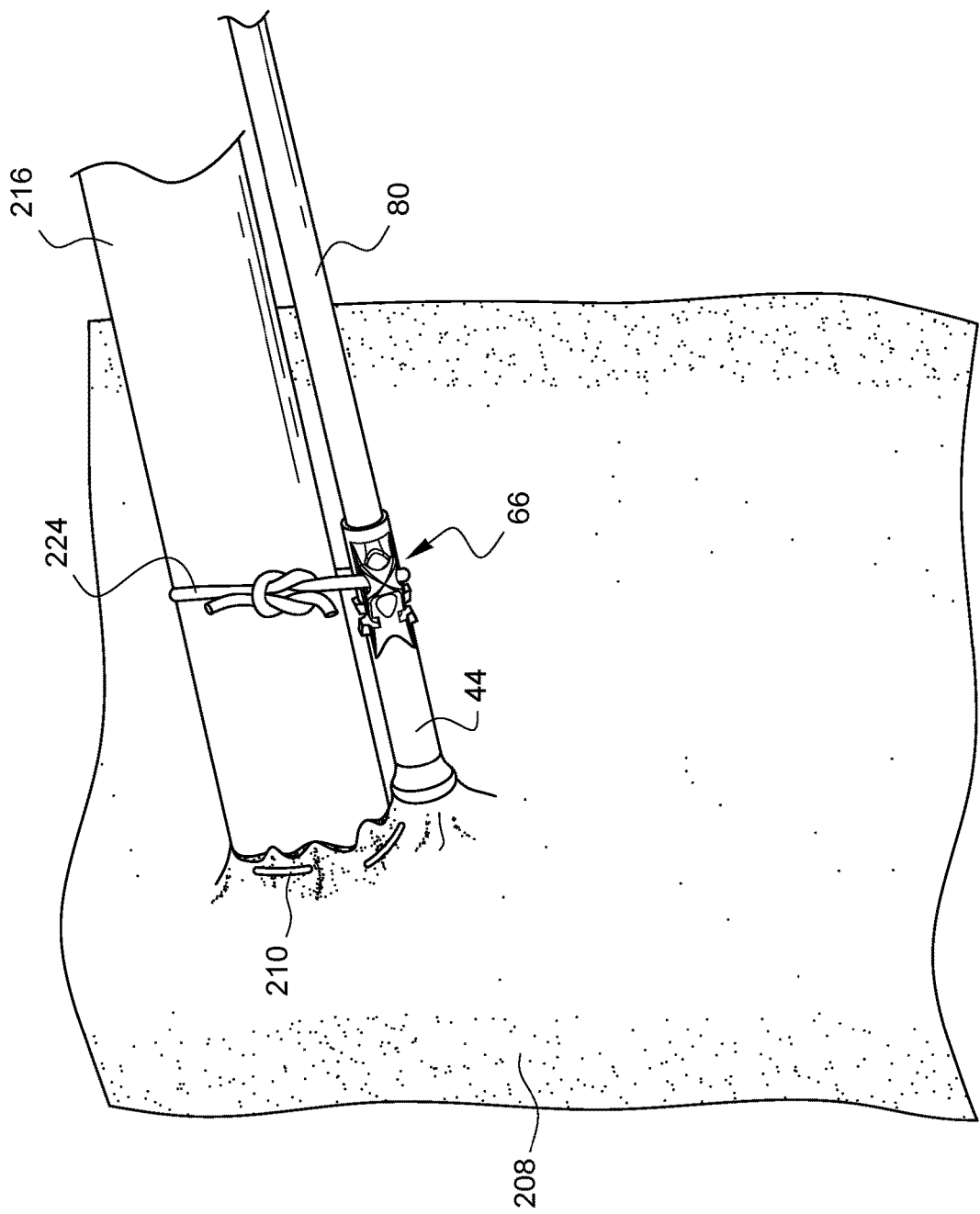

FIGS. 25A-25G illustrate a method of cannulation using the assembly 78 previously discussed with regard to FIG. 9. By way of review, the assembly 78 has a distal tip 44 crimped onto a tube 80. A snare 82 protrudes from the distal tip 44 and passes through the distal tip 44, through the tube 80, and out the proximal end of the tube 80 where it is coupled to a handle 84. As shown in FIG. 25, a suture 210 has been stitched through the wall of a vessel 208, such as, but not limited to an aorta, in a purse string suture formation as is known to those skilled in the art. The ends 212, 214 of the suture 210 may be placed through the snare 82, and the handle 84 may be pulled to draw the suture ends 212, 214 through the assembly 78 such that the suture ends exit the proximal end of tube 80 as is shown in FIG. 25B. As illustrated in FIG. 25C, the tip of a cannula 216 may be pressed into the space 218 on the vessel 208 inside the purse string suture stitches 210. Eventually, the cannula 216 will pierce the vessel 208 as illustrated in FIG. 25D. At this point, as also illustrated in FIG. 25D, the tube 80 may be held steady while the suture ends 212, 214 are pulled in a proximal direction 220. This will initially cause the distal tip 44 to contact the vessel 208 if it already was not, and then, as more tension is applied, the suture 210 will be drawn into the distal tip 44, causing the purse string to cinch the vessel 208 around the cannula 216 as illustrated in FIG. 25E and FIG. 25F. A desired tension can be maintained by using a clamp 222 to clamp the suture ends 212, 214 directly where they exit the tube 80 as shown in FIG. 25E. Alternatively, the desired tension can be maintained by using the clamp 222 to clamp the proximal end of tube 80 which indirectly clamps the suture ends 212, 214 before they exit the tube 80 as shown in FIG. 25F. In either case, the vessel 208 is protected from damage by the flared end of the distal tip 44. Finally, and optionally, the distal tip 44 may be secured to the cannula 216 by another suture 224 which can be passed through one or more of the anchor channels, such as anchor channel 66 and knotted around the cannula 216 as shown in FIG. 25G in order to help keep the distal tip 44 and the tube 80 from tilting away from the cannula 216 and possibly interfering with other areas of surgical activity during the same surgical procedure.

Figure 26:
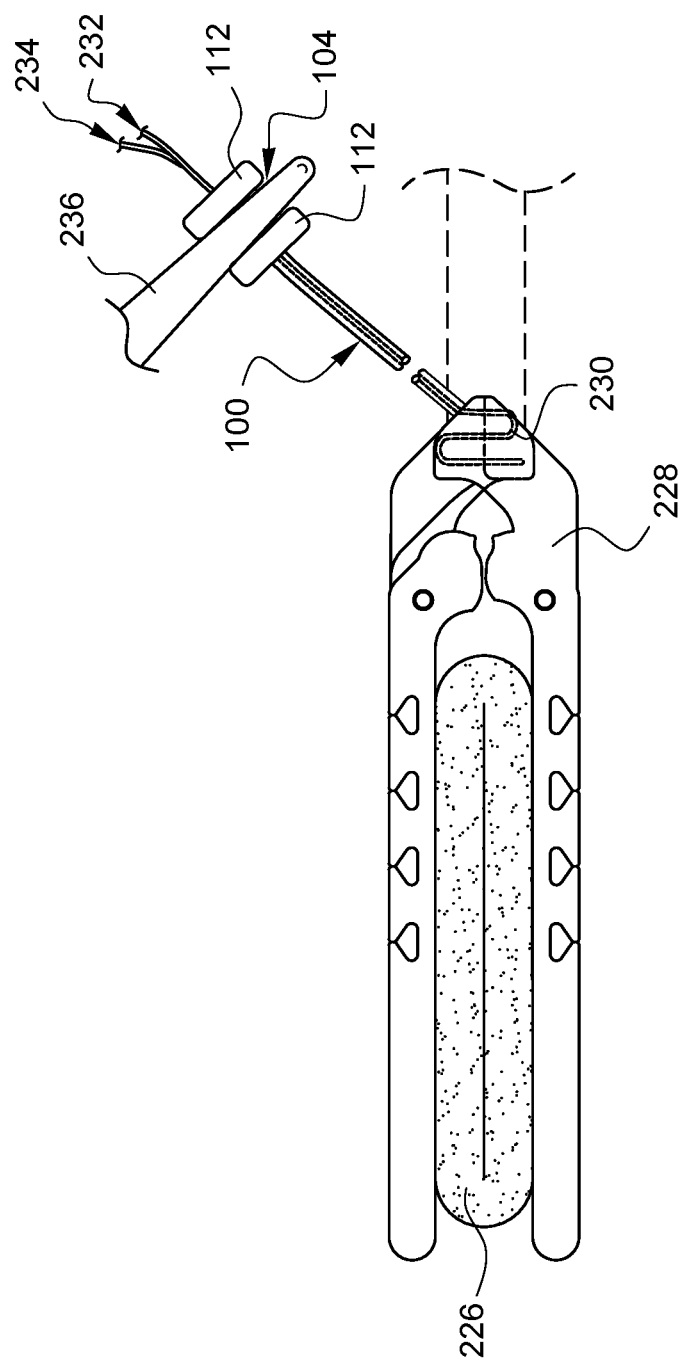
FIG. 26 illustrates the device of FIGS. 11-13 in a usage example.

Although the suture securing tube devices described herein are highly useful when used with tissue, such devices are also helpful when used to securing surgical apparatus, such as, but not limited to a clamp 228 as illustrated in FIG. 26. The clamp 228 is illustrated as having been applied to a vessel 226, such as might be done with an aortic cross clamp. A suture 230 has been threaded through control arms of the clamp and the suture ends 232, 234 have been drawn up through a suture tube having a flexible collar 104 as has been discussed previously. By tensioning the suture ends 232, 234, the clamp squeezes the vessel 226 and the clamp force can be maintained by applying a separate clamp 236 to the flexible collar 104 between the side guides 112. This can be very useful because the clamp 228 may be located in a difficult to reach location via a minimally invasive opening, but the tension can clamping can be controlled externally to the patient where there is a lot of space.

Various advantages of a suture securing tube have been discussed above. Embodiments discussed herein have been described by way of example in this specification. It will be apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A distal tip for a suture securing tube, comprising:
a flared distal end;
a distal opening in the flared distal end;
a tube interface opening in a proximal end;
a channel coupling the distal opening to the tube interface opening; and
one or more crimp windows adjacent to the proximal end of the distal tip and in communication between an outer surface of the distal tip and the channel.

2. The distal tip of claim 1, further comprising:
one or more crimp directors adjacent to the one or more crimp windows.

3. The distal tip of claim 1, further comprising:
one or more anchor channels adjacent to the proximal end of the distal tip.

4. The distal tip of claim 3, wherein the one or more anchor channels are not parallel to a longitudinal axis of the distal tip.

5. The distal tip of claim 3, further comprising a first anchor channel and a second anchor channel wherein the first anchor channel intersects the second anchor channel.

6. The distal tip of claim 1, further comprising threads on an outer surface of the proximal end of the distal tip.

7. The distal tip of claim 1, further comprising threads on an inner surface of the flared distal end of the distal tip.

8. The distal tip of claim 1, further comprising a protrusion on an outer surface of the proximal end of the distal tip.

9. The distal tip of claim 1, further comprising a detent on an inner surface of the flared distal end of the distal tip.

* * * * *